(12) United States Patent
Conway et al.

(10) Patent No.: US 7,469,844 B2
(45) Date of Patent: Dec. 30, 2008

(54) DIFFUSION DEVICE AND METHOD OF DIFFUSING

(75) Inventors: Simon M. Conway, Burlington, WI (US); Thomas Jaworski, Racine, WI (US); Heather R. Schramm, Whitewater, WI (US); Scott D. Walter, Twin Lakes, WI (US); Jeffrey L. Crull, McFarland, WI (US); Lawrence J. Fenske, Madison, WI (US); Jonathan M. Mick, Marshall, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 523 days.

(21) Appl. No.: 11/131,718

(22) Filed: May 18, 2005

(65) Prior Publication Data

US 2005/0205916 A1      Sep. 22, 2005

Related U.S. Application Data

(63) Continuation-in-part of application No. PCT/US03/36090, filed on Nov. 10, 2003.

(60) Provisional application No. 60/670,519, filed on Apr. 12, 2005, provisional application No. 60/425,061, filed on Nov. 8, 2002.

(51) Int. Cl.
*B05B 1/08* (2006.01)

(52) U.S. Cl. ............... 239/102.2; 239/66; 239/145; 239/305; 239/326; 261/DIG. 65; 261/DIG. 88; 422/123

(58) Field of Classification Search ............ 239/102.1, 239/102.2, 145, 303–305, 326, 332, 338, 239/66; 261/99, 104, DIG. 65, DIG. 88; 422/123; 128/200.16, 204.13

See application file for complete search history.

(56) References Cited

U.S. PATENT DOCUMENTS

| 1,204,934 | A | 11/1916 | Burford et al. |
|---|---|---|---|
| 1,763,374 | A | 6/1930 | Schrader |
| 1,829,714 | A | 10/1931 | McElroy et al. |
| 1,947,752 | A | 2/1934 | Benesh |
| 2,084,682 | A | 6/1937 | Guenot |
| 2,094,161 | A | 9/1937 | Paddock |
| 2,103,609 | A | 12/1937 | Bradburn |
| 2,221,876 | A | 11/1940 | Mackin |
| 2,301,691 | A | 11/1942 | Ellinger et al. |

(Continued)

FOREIGN PATENT DOCUMENTS

AU          2005101048          2/2006

(Continued)

OTHER PUBLICATIONS

Int'l Search Report dated Apr. 23, 2004 PCT/US2003/36090.

(Continued)

*Primary Examiner*—Steven J Ganey

(57) ABSTRACT

A diffusion device comprises a bottom portion having a bottom cover disposed thereon. The device further includes a top portion having a top cover disposed atop the bottom portion and a pump assembly disposed between the top cover and the bottom cover. First, second, and third arm portions extend from the pump assembly, wherein the first, second, and third arm portions include first, second, and third piezoelectric devices, respectively, attached thereto.

19 Claims, 28 Drawing Sheets

U.S. PATENT DOCUMENTS

| | | |
|---|---|---|
| 2,555,047 A | 5/1951 | Logue |
| 2,600,877 A | 6/1952 | Jeffree |
| 2,608,436 A | 8/1952 | Baughman |
| 2,686,944 A | 8/1954 | Gubelin |
| 2,741,004 A | 4/1956 | Williams |
| 2,905,049 A | 9/1959 | Laube |
| D191,396 S | 9/1961 | Weber, III |
| 3,118,610 A | 1/1964 | Techler |
| 3,172,604 A | 3/1965 | Brock |
| 3,301,486 A | 1/1967 | Brock |
| 3,370,571 A | 2/1968 | Kanpp |
| 3,370,951 A | 2/1968 | Knapp |
| 3,383,178 A | 5/1968 | Dietz |
| 3,410,488 A | 11/1968 | Sugimura |
| 3,447,505 A | 6/1969 | Wagner |
| 3,612,356 A | 10/1971 | McVey |
| 3,628,829 A | 12/1971 | Heilig |
| 3,655,135 A | 4/1972 | Altman et al. |
| 3,711,023 A | 1/1973 | Smith |
| 3,763,888 A | 10/1973 | Duecker |
| 3,812,996 A | 5/1974 | Bunnell |
| 3,844,057 A | 10/1974 | Johnson |
| 3,864,080 A | 2/1975 | Valbona et al. |
| 3,917,396 A | 11/1975 | Donohue et al. |
| 3,972,473 A | 8/1976 | Harrison |
| 4,006,841 A | 2/1977 | Alticosalian |
| 4,084,732 A | 4/1978 | Dearling |
| 4,229,415 A | 10/1980 | Bryson |
| 4,235,373 A | 11/1980 | Clark |
| 4,301,093 A * | 11/1981 | Eck .......... 239/102.2 |
| 4,346,059 A | 8/1982 | Spector |
| 4,391,390 A | 7/1983 | Howard |
| 4,433,796 A | 2/1984 | Brooks, Jr. |
| 4,456,176 A | 6/1984 | Agius |
| 4,545,396 A | 10/1985 | Miller et al. |
| 4,556,539 A | 12/1985 | Spector |
| 4,580,721 A | 4/1986 | Coffee et al. |
| 4,603,030 A | 7/1986 | McCarthy |
| 4,614,300 A | 9/1986 | Falcoff |
| 4,629,164 A | 12/1986 | Sommerville |
| 4,629,604 A | 12/1986 | Spector |
| 4,680,060 A | 7/1987 | Gupta et al. |
| 4,695,434 A | 9/1987 | Spector |
| 4,755,404 A | 7/1988 | Collette |
| 4,790,479 A | 12/1988 | Matsumoto et al. |
| 4,804,821 A | 2/1989 | Glucksman |
| 4,846,403 A | 7/1989 | Mivelaz |
| 4,852,802 A | 8/1989 | Iggulden et al. |
| 4,870,991 A | 10/1989 | McMillan et al. |
| 4,878,615 A | 11/1989 | Losi |
| 4,881,568 A | 11/1989 | Ho |
| 4,889,285 A | 12/1989 | Locko |
| 4,893,615 A | 1/1990 | Khabirova |
| 4,901,890 A | 2/1990 | Mivelaz |
| 4,905,112 A | 2/1990 | Rhodes |
| 4,913,034 A | 4/1990 | Ripple et al. |
| 4,915,301 A | 4/1990 | Munteanu |
| 4,917,301 A | 4/1990 | Munteanu |
| 5,011,632 A | 4/1991 | Yano et al. |
| 5,021,701 A | 6/1991 | Takahashi et al. |
| 5,022,585 A | 6/1991 | Burgess |
| 5,023,020 A | 6/1991 | Machida et al. |
| 5,038,972 A | 8/1991 | Muderlak et al. |
| 5,050,798 A | 9/1991 | Sullivan |
| 5,071,621 A | 12/1991 | Tokuhiro et al. |
| 5,074,438 A | 12/1991 | Ingram |
| 5,086,978 A | 2/1992 | Fertig |
| 5,097,375 A | 3/1992 | Khan |
| 5,105,133 A | 4/1992 | Yang |
| 5,111,477 A | 5/1992 | Muderlak |
| 5,115,975 A | 5/1992 | Shilling |
| 5,133,498 A | 7/1992 | Sealy et al. |
| 5,152,397 A | 10/1992 | Mayled |
| 5,163,616 A | 11/1992 | Bernarducci et al. |
| 5,167,877 A | 12/1992 | Pai |
| 5,175,791 A | 12/1992 | Muderlak et al. |
| 5,178,327 A | 1/1993 | Palamand et al. |
| 5,186,869 A | 2/1993 | Stumpf et al. |
| 5,192,342 A | 3/1993 | Baron et al. |
| 5,193,744 A | 3/1993 | Goldstein |
| 5,201,025 A | 4/1993 | Landesberg |
| 5,212,672 A | 5/1993 | Loisch et al. |
| 5,227,068 A | 7/1993 | Runyon |
| 5,230,837 A | 7/1993 | Babasade |
| 5,234,162 A | 8/1993 | Sullivan |
| 5,314,619 A | 5/1994 | Runyon |
| 5,314,669 A | 5/1994 | Hamilton |
| 5,321,669 A | 6/1994 | Thayer et al. |
| 5,342,584 A | 8/1994 | Fritz et al. |
| 5,343,747 A | 9/1994 | Rosen |
| 5,364,027 A | 11/1994 | Kuhn |
| 5,377,363 A | 1/1995 | Shieh |
| RE34,847 E | 2/1995 | Muderlak et al. |
| 5,398,070 A | 3/1995 | Lee |
| 5,402,517 A | 3/1995 | Gillet et al. |
| D359,346 S | 6/1995 | Martin |
| 5,437,410 A | 8/1995 | Babasade |
| 5,449,117 A | 9/1995 | Muderlak et al. |
| 5,518,790 A | 5/1996 | Huber et al. |
| 5,524,609 A | 6/1996 | Krull |
| 5,534,229 A | 7/1996 | Nomura et al. |
| 5,565,148 A | 10/1996 | Pendergrass, Jr. |
| 5,591,409 A | 1/1997 | Watkins |
| 5,647,052 A | 7/1997 | Patel et al. |
| 5,658,387 A | 8/1997 | Reardon et al. |
| 5,660,330 A | 8/1997 | Scott |
| 5,666,987 A | 9/1997 | Combs |
| 5,695,692 A | 12/1997 | Kennedy |
| 5,724,256 A | 3/1998 | Lee et al. |
| 5,725,472 A | 3/1998 | Weathers |
| 5,727,186 A | 3/1998 | Shervington et al. |
| 5,734,590 A | 3/1998 | Tebbe |
| 5,762,268 A | 6/1998 | Shervington et al. |
| 5,772,074 A | 6/1998 | Dial et al. |
| 5,776,561 A | 7/1998 | Lindauer et al. |
| 5,805,768 A | 9/1998 | Schwartz et al. |
| 5,810,201 A | 9/1998 | Besse et al. |
| 5,816,446 A | 10/1998 | Steindorf et al. |
| 5,832,320 A | 11/1998 | Wittek |
| 5,881,714 A | 3/1999 | Yokoi et al. |
| 5,884,808 A | 3/1999 | Muderlak et al. |
| 5,887,118 A | 3/1999 | Huffman et al. |
| 5,894,841 A | 4/1999 | Voges |
| 5,898,475 A | 4/1999 | Martin |
| 5,899,381 A | 5/1999 | Gordon et al. |
| 5,899,382 A | 5/1999 | Hayes et al. |
| 5,908,231 A | 6/1999 | Huff |
| 5,924,597 A | 7/1999 | Lynn |
| 5,938,117 A | 8/1999 | Ivri |
| 5,949,522 A | 9/1999 | Manne |
| 5,972,290 A | 10/1999 | De Sousa |
| 5,975,675 A | 11/1999 | Kim |
| 6,000,658 A | 12/1999 | McCall, Jr. |
| 6,003,727 A | 12/1999 | Marshall |
| 6,013,231 A | 1/2000 | Zaunbrecher et al. |
| 6,039,212 A | 3/2000 | Singh |
| 6,044,202 A | 3/2000 | Junkel |
| 6,053,738 A | 4/2000 | Ivey, Jr. |
| 6,123,935 A | 9/2000 | Wefler et al. |
| 6,136,277 A | 10/2000 | Nardini |
| 6,189,810 B1 | 2/2001 | Nerushai et al. |
| 6,196,218 B1 | 3/2001 | Voges |
| 6,231,032 B1 | 5/2001 | Ivey, Jr. |
| 6,234,455 B1 | 5/2001 | Wittek |

| | | |
|---|---|---|
| 6,241,944 B1 | 6/2001 | Budman |
| 6,254,065 B1 | 7/2001 | Ehrensperger et al. |
| 6,254,248 B1 | 7/2001 | McAuley et al. |
| 6,279,836 B1 | 8/2001 | Toetschinger et al. |
| 6,293,474 B1 | 9/2001 | Helf et al. |
| 6,296,196 B1 | 10/2001 | Denen et al. |
| D451,990 S | 12/2001 | Millet |
| 6,328,287 B2 | 12/2001 | Wittek |
| 6,338,818 B2 | 1/2002 | Budman |
| 6,341,732 B1 | 1/2002 | Martin et al. |
| 6,357,726 B1 | 3/2002 | Watkins |
| 6,371,451 B1 | 4/2002 | Choi |
| 6,382,522 B2 | 5/2002 | Tomkins et al. |
| 6,390,453 B1 | 5/2002 | Frederickson et al. |
| 6,406,004 B1 | 6/2002 | Ude |
| 6,409,093 B2 | 6/2002 | Ulczynski et al. |
| 6,439,474 B2 | 8/2002 | Denen |
| D463,437 S | 9/2002 | Bush et al. |
| 6,446,583 B2 | 9/2002 | Vieira |
| 6,448,219 B1 | 9/2002 | Cooper |
| 6,450,419 B1 | 9/2002 | Martens, III et al. |
| D464,130 S | 10/2002 | Denham et al. |
| 6,487,367 B2 | 11/2002 | Vieira |
| 6,501,906 B2 | 12/2002 | Vieira |
| 6,502,762 B2 | 1/2003 | Tuttobene, Jr. |
| 6,505,759 B2 | 1/2003 | Holyfield |
| 6,511,531 B1 | 1/2003 | Cartellone |
| 6,520,826 B2 | 2/2003 | Spector |
| 6,533,193 B2 | 3/2003 | White |
| 6,536,746 B2 | 3/2003 | Watkins |
| 6,542,442 B2 | 4/2003 | Kaslon |
| 6,554,203 B2 | 4/2003 | Hess et al. |
| 6,556,272 B1 | 4/2003 | Du et al. |
| 6,563,091 B2 | 5/2003 | Vieira |
| 6,568,659 B2 | 5/2003 | Hugon |
| 6,569,387 B1 | 5/2003 | Furner et al. |
| 6,581,915 B2 | 6/2003 | Bartsch et al. |
| 6,584,633 B2 | 7/2003 | Chute et al. |
| 6,592,104 B2 | 7/2003 | Cox |
| 6,602,475 B1 | 8/2003 | Chiao |
| 6,603,924 B2 | 8/2003 | Brown et al. |
| 6,610,254 B1 | 8/2003 | Furner et al. |
| 6,619,559 B2 | 9/2003 | Wohrle |
| 6,654,664 B1 | 11/2003 | Chiao |
| 6,661,967 B2 | 12/2003 | Levine et al. |
| 6,706,988 B1 | 3/2004 | Helf et al. |
| 6,712,287 B1 | 3/2004 | Le Pesant et al. |
| 6,713,024 B1 | 3/2004 | Arnell et al. |
| 6,714,725 B2 | 3/2004 | Grone et al. |
| 6,728,478 B2 | 4/2004 | Cox et al. |
| 6,769,905 B2 | 8/2004 | Gray et al. |
| 6,783,117 B2 | 8/2004 | Wohrle |
| 6,790,011 B1 | 9/2004 | Le Pesant et al. |
| 6,790,408 B2 | 9/2004 | Whitby et al. |
| 6,792,199 B2 | 9/2004 | Levine et al. |
| 6,793,149 B2 | 9/2004 | Schramm et al. |
| D497,288 S | 10/2004 | McGuyer |
| 6,802,460 B2 | 10/2004 | Hess et al. |
| 6,803,987 B2 | 10/2004 | Manne |
| 6,810,204 B2 | 10/2004 | Grone et al. |
| 6,834,847 B2 | 12/2004 | Bartsch et al. |
| 6,842,218 B1 | 1/2005 | Manne |
| 6,843,430 B2 | 1/2005 | Boticki et al. |
| 6,859,615 B2 | 2/2005 | Yip et al. |
| 6,871,794 B2 | 3/2005 | McEwen |
| 6,896,196 B2 | 5/2005 | Vieira |
| 6,912,355 B2 | 6/2005 | Vieira |
| 6,913,208 B2 | 7/2005 | Tabata et al. |
| 6,913,733 B2 | 7/2005 | Hardy et al. |
| 6,921,024 B2 | 7/2005 | Donnelly et al. |
| 7,011,795 B2 | 3/2006 | Thompson et al. |
| 7,021,494 B2 | 4/2006 | Mazooji et al. |
| 7,223,166 B1 | 5/2007 | Wiseman, Sr. et al. |
| 2001/0048037 A1 | 12/2001 | Bell et al. |
| 2002/0018181 A1 | 2/2002 | Manne |
| 2002/0066798 A1 | 6/2002 | Laudamiel-Pellet et al. |
| 2002/0068009 A1 | 6/2002 | Laudamiel-Pellet et al. |
| 2002/0068010 A1 | 6/2002 | Laudamiel-Pellet et al. |
| 2002/0114744 A1 | 8/2002 | Chiao et al. |
| 2002/0158351 A1 | 10/2002 | Wohrle |
| 2002/0159916 A1 | 10/2002 | Whitby et al. |
| 2003/0006303 A1 | 1/2003 | Ivey et al. |
| 2003/0102384 A1 | 6/2003 | Walter et al. |
| 2003/0107139 A1 | 6/2003 | Wohrle |
| 2003/0138241 A1 | 7/2003 | Pedrotti et al. |
| 2003/0164557 A1 | 9/2003 | Cheng et al. |
| 2003/0168524 A1 | 9/2003 | Hess et al. |
| 2003/0168751 A1 | 9/2003 | Bartsch et al. |
| 2003/0175148 A1 | 9/2003 | Kvietok et al. |
| 2003/0192959 A1 | 10/2003 | Hess et al. |
| 2003/0206834 A1 | 11/2003 | Chiao et al. |
| 2004/0007737 A1 | 1/2004 | Kvietok et al. |
| 2004/0007787 A1 | 1/2004 | Kvietok et al. |
| 2004/0009103 A1 | 1/2004 | Westring |
| 2004/0016818 A1 | 1/2004 | Murdell et al. |
| 2004/0028551 A1 | 2/2004 | Kvietok et al. |
| 2004/0033067 A1 | 2/2004 | He et al. |
| 2004/0033171 A1 | 2/2004 | Kvietok et al. |
| 2004/0071456 A1 | 4/2004 | Levine et al. |
| 2004/0131509 A1 | 7/2004 | He et al. |
| 2004/0195372 A1 | 10/2004 | Yoshikawa et al. |
| 2004/0217188 A1 | 11/2004 | McEwen |
| 2004/0217197 A1 | 11/2004 | Mazooji et al. |
| 2004/0223871 A1 | 11/2004 | Woo et al. |
| 2004/0223891 A1 | 11/2004 | Brown |
| 2004/0223943 A1 | 11/2004 | Woo et al. |
| 2004/0241053 A1 | 12/2004 | Thompson et al. |
| 2004/0247301 A1 | 12/2004 | Yip et al. |
| 2004/0265164 A1 | 12/2004 | Woo et al. |
| 2005/0001337 A1 | 1/2005 | Pankhurst et al. |
| 2005/0028819 A1 | 2/2005 | Manne |
| 2005/0147523 A1 | 7/2005 | Laudamiel-Pellet et al. |
| 2005/0147539 A1 | 7/2005 | Laudamiel-Pellet et al. |
| 2005/0161522 A1 | 7/2005 | Kvietok et al. |
| 2005/0201944 A1 | 9/2005 | Kvietok et al. |
| 2005/0211790 A1 | 9/2005 | Kvietok et al. |
| 2005/0214158 A1 | 9/2005 | Kvietok et al. |
| 2006/0018786 A1 | 1/2006 | Tolman et al. |
| 2006/0018803 A1 | 1/2006 | Kvietok et al. |
| 2006/0067859 A1 | 3/2006 | Laudamiel-Pellet et al. |
| 2006/0097065 A1 | 5/2006 | Kvietok et al. |
| 2006/0097066 A1 | 5/2006 | Kvietok et al. |
| 2006/0193611 A1 | 8/2006 | Ballesteros et al. |

FOREIGN PATENT DOCUMENTS

| | | |
|---|---|---|
| CA | 2222838 | 1/1997 |
| DE | 199 38 405 | 2/2001 |
| EP | 295 129 | 12/1988 |
| EP | 0 714 709 | 6/1996 |
| EP | 1 108 358 | 6/2001 |
| EP | 1 195 169 | 4/2002 |
| EP | 1 247 446 | 10/2002 |
| EP | 1 247 447 | 10/2002 |
| EP | 1 184 083 | 3/2003 |
| EP | 1 303 316 | 4/2003 |
| EP | 1 303 317 | 4/2003 |
| EP | 1 303 318 | 4/2003 |
| EP | 1 303 319 | 4/2003 |
| EP | 1 469 131 | 10/2004 |
| GB | 2 253 732 | 9/1992 |
| GB | 2 401 047 | 11/2004 |
| GB | 2 401 790 | 11/2004 |
| GB | 2 418 859 | 4/2006 |
| JP | 04024029 | 1/1992 |
| JP | 404267740 A | 9/1992 |

| | | |
|---|---|---|
| JP | 404354950 A | 12/1992 |
| JP | 06 320083 | 11/1994 |
| JP | 408336578 A | 12/1996 |
| JP | 11-000391 | 1/1999 |
| WO | WO 00/12143 | 3/2000 |
| WO | WO 00/53301 | 9/2000 |
| WO | WO 00/60486 | 10/2000 |
| WO | WO 00/60489 | 10/2000 |
| WO | WO 02/09772 | 2/2002 |
| WO | WO 02/09773 | 2/2002 |
| WO | WO 02/09776 | 2/2002 |
| WO | WO 02/09779 | 2/2002 |
| WO | WO 02/32472 | 4/2002 |
| WO | WO 03/068412 | 8/2003 |
| WO | WO 03/098971 | 11/2003 |
| WO | WO 03/099458 | 12/2003 |
| WO | WO 03/102291 | 12/2003 |
| WO | WO 03/105652 | 12/2003 |
| WO | WO 2004/007008 | 1/2004 |
| WO | WO 2004/009142 | 1/2004 |
| WO | WO 2004/011836 | 2/2004 |
| WO | WO 2004/043502 | 5/2004 |
| WO | WO 2004/071935 | 8/2004 |
| WO | WO 2004/093927 | 11/2004 |
| WO | WO 2004/093928 | 11/2004 |
| WO | WO 2004/093929 | 11/2004 |
| WO | WO 2004/105813 | 12/2004 |
| WO | WO 2004/105814 | 12/2004 |
| WO | WO 2004/105815 | 12/2004 |
| WO | WO 2004/105878 | 12/2004 |
| WO | WO 2005/011761 | 2/2005 |
| WO | WO 2006/105347 | 10/2006 |

OTHER PUBLICATIONS

Int'l Search Report & Written Opinion dated Nov. 7, 2005 PCT/US2005/023211.

Yankee Candle web page http://www.yankeecandle.com/cgi-bin/ycbvp/product_detail.jsp?oid=3001476 1 page, printed May 15, 2007.

SCJ Create a Scent web page http://www.glade.com/glade-plug-ins/, 3 pages, printed May 16, 2007.

International Search Report and Written Opinion dated Sep. 1, 2006, Appl. No. PCT/US/2006/013841.

International Preliminary Report on Patentability and Written Opinion in PCT/US2006/013600 dated Oct. 25, 2007.

* cited by examiner

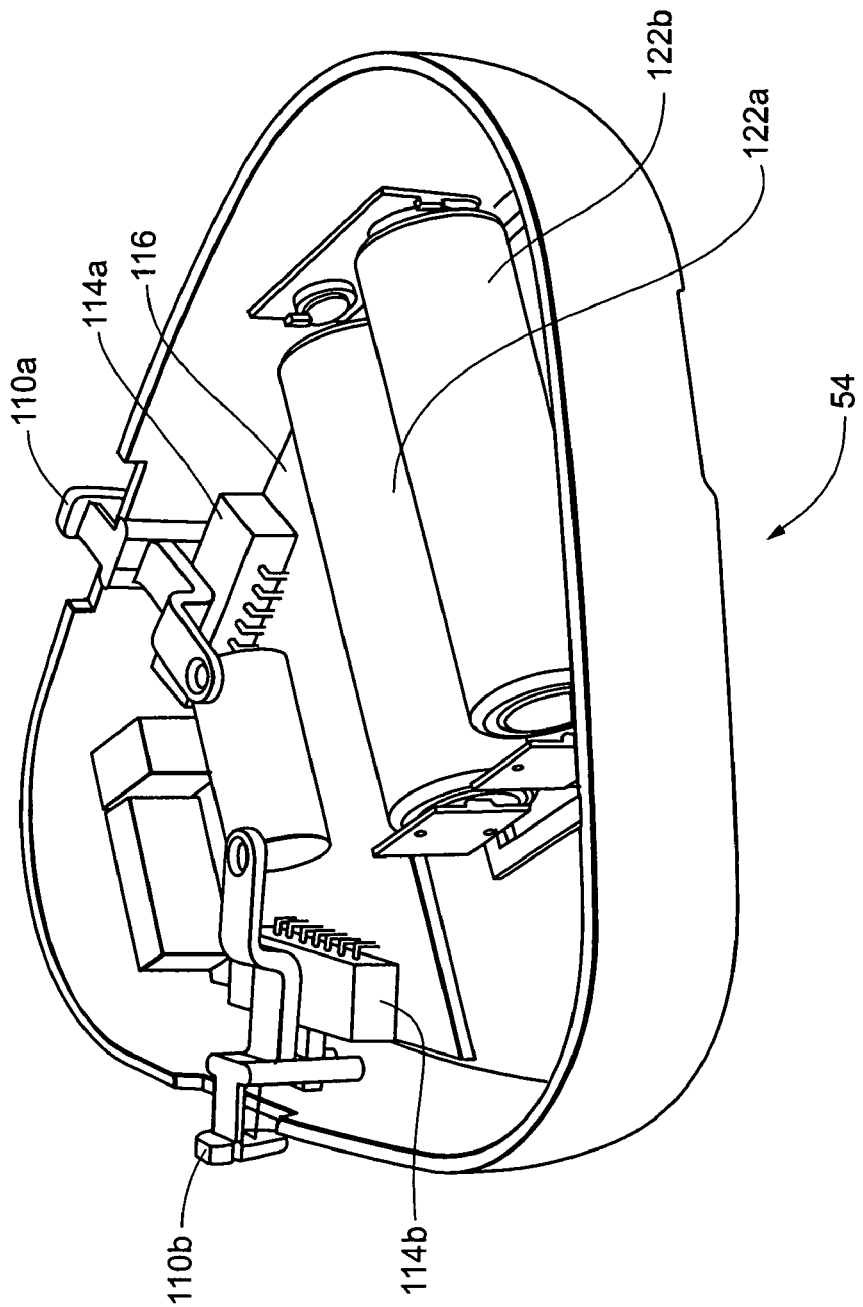

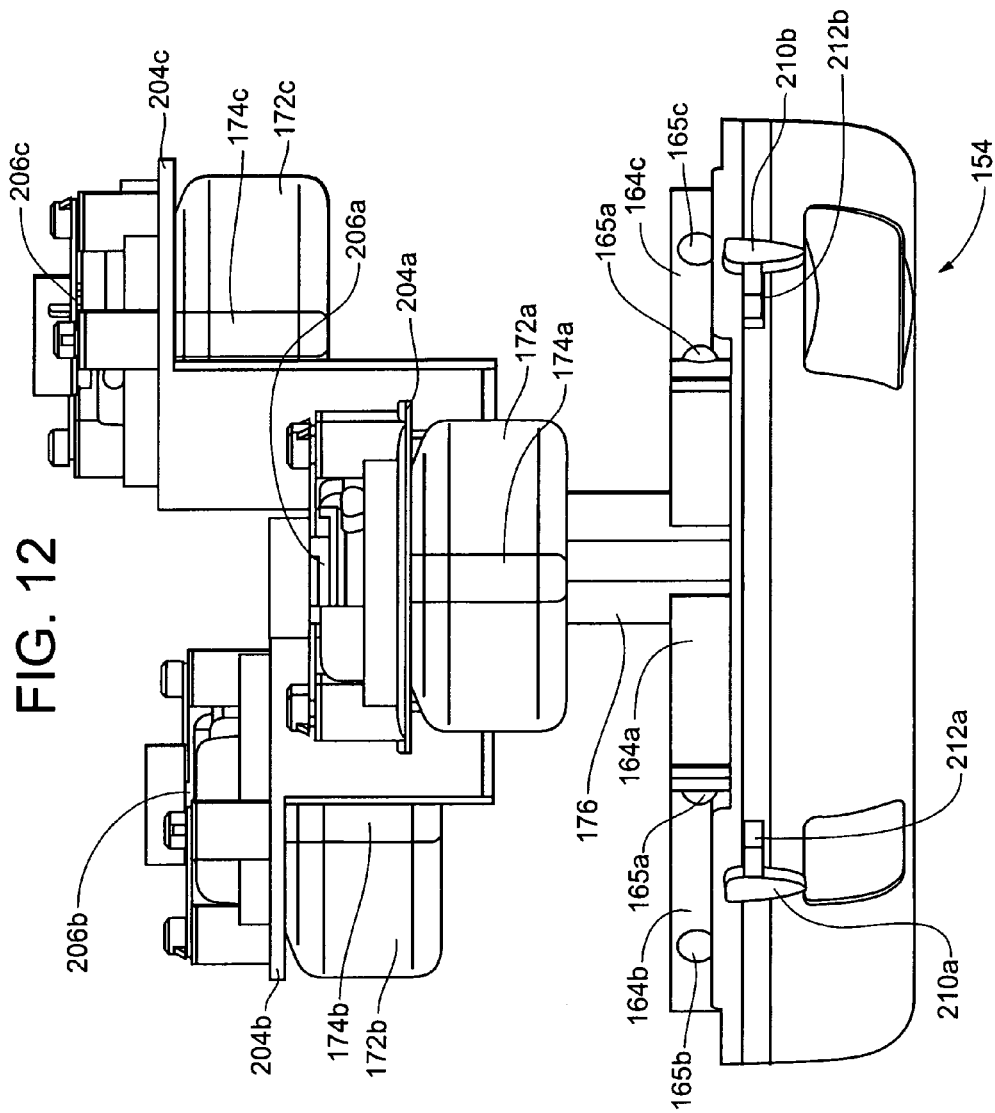

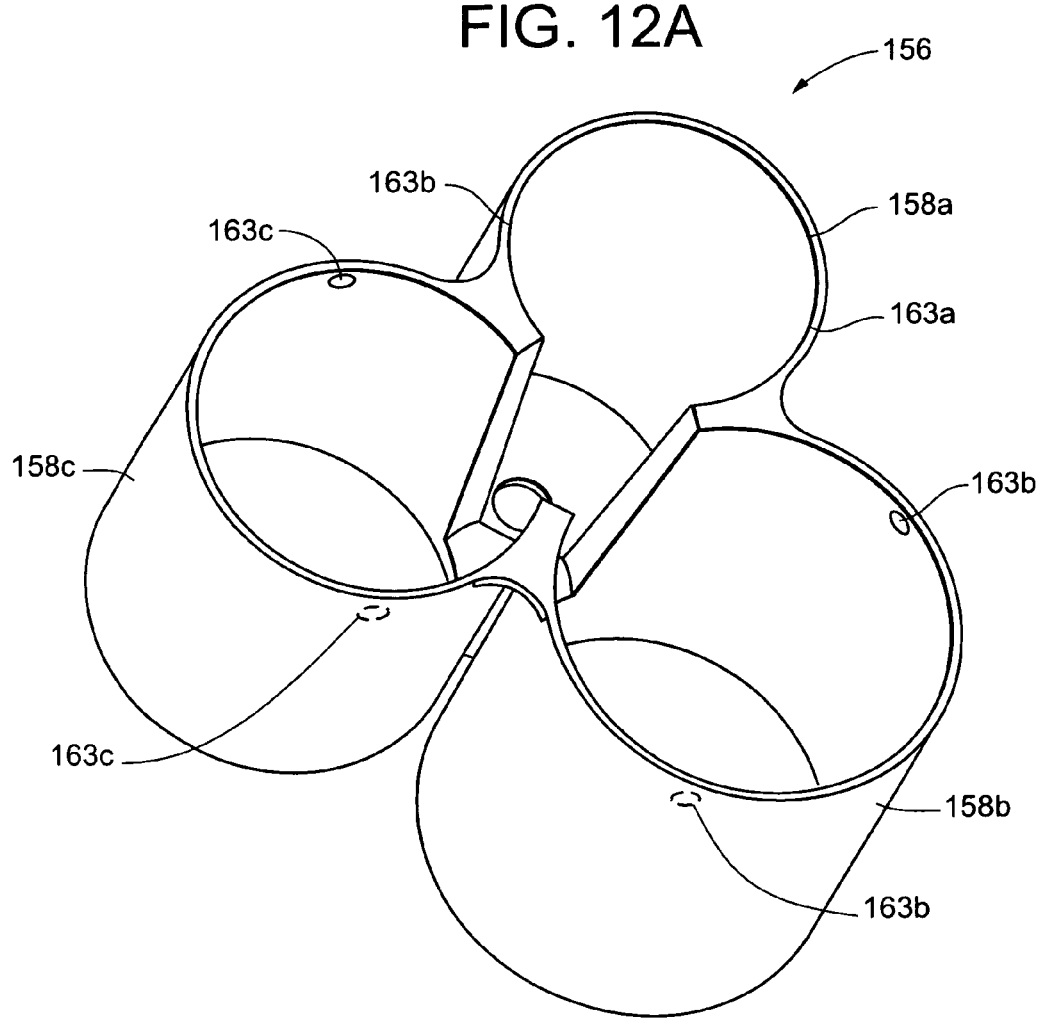

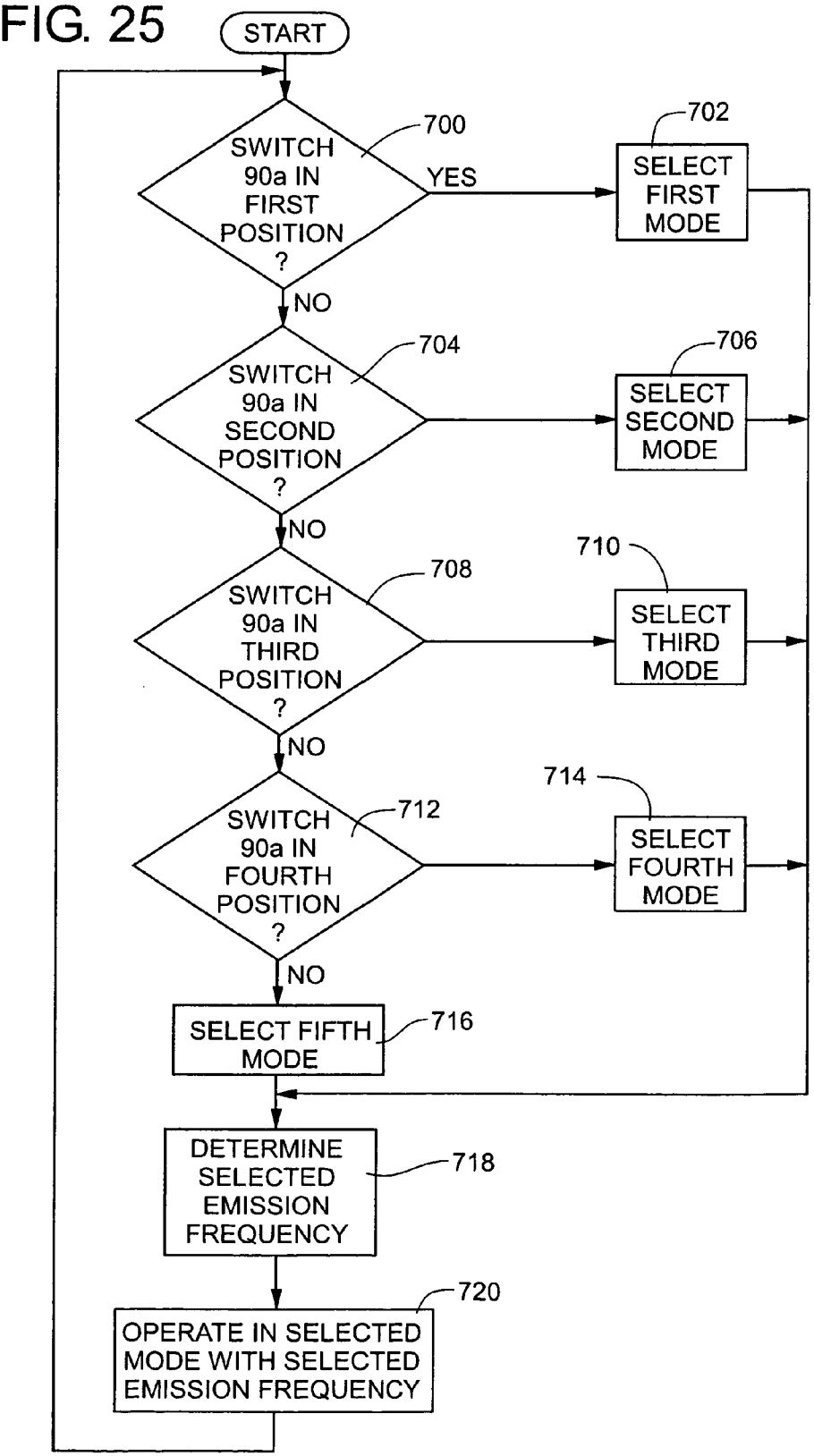

DIFFUSION DEVICE AND METHOD OF DIFFUSING

CROSS REFERENCE TO RELATED APPLICATIONS

This application is a continuation-in-part of Application No. PCT/US2003/036090, filed Nov. 10, 2003, which claims priority to U.S. Provisional Application Ser. No. 60/425,061, filed Nov. 8, 2002, and U.S. Provisional Application Ser. No. 60/670,519, filed Apr. 12, 2005. This application claims priority to all such previous applications, and such applications are hereby incorporated herein by reference in their entireties.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Technical Field

The present disclosure relates to diffusion devices, and more particularly, to diffusion devices for emitting more than one active material therefrom.

2. Description of the Background

A multitude of active material diffusion devices or diffusers exist in the marketplace. Many of such devices are passive devices that require only ambient air flow to disperse the liquid active material therein. Other devices are battery-powered or receive household power via a plug extending from the device. A cord may be coupled between the plug and the device, or the plug may be mounted directly on the device.

Various means for dispensing active materials from diffusion devices are also known in the art. For example, some diffusion devices include a heating element for heating an active material to promote vaporization thereof. Other diffusion devices employ a fan or blower to generate air flow to direct active material out of the diffusion device into the surrounding environment. In another type of diffusion device, active material may be emitted from the device using a bolus generator that delivers a pulse of air to eject a scent ring. Still other diffusion devices dispense active materials utilize ultrasonic means to dispense active materials therefrom.

In one example a diffusion device includes two heaters for dispersion of fragrances. The device includes a housing, a plug extending from the housing for insertion into an outlet, and two containers having fragrances therein and wicks extending therefrom to absorb fragrances from the containers. Each of the heaters is disposed adjacent one of the wicks to heat the respective wick to vaporize the fragrances therein. Optionally, a CPU controlled by internal software may first activate a first of the two heaters for a predetermined period of time. After the period of time expires, the CPU deactivates the first heater and thereafter activates the second heater.

Other diffusion devices include a housing having a cavity for receiving a cartridge. The cartridge generally has a plurality of scent elements disposed on a rotatable disk. A blower is mounted in the housing to generate airflow by passing air across a scent element and out an aperture in the housing. The housing further includes rotating means that rotate the rotatable disk, thereby rotating the scent elements thereon. The device diffuses a first scent for a predetermined time period and thereafter rotates the disk to a second scent and diffuses the second scent for the predetermined time period. This process repeats itself until the last scent element is diffused for the time period and then the disk is rotated to a home position.

Piezoelectrically actuated vibratory type liquid atomization apparatuses are described in Helf et al. U.S. Pat. No. 6,293,474, Martin et al. U.S. Pat. No. 6,341,732, Tomkins et al. U.S. Pat. No. 6,382,522, Martens, III et al. U.S. Pat. No. 6,450,419, Helf et al. U.S. Pat. No. 6,706,988, and Boticki et al. U.S. Pat. No. 6,843,430, all of which are assigned to the assignee of the present application and which are hereby incorporated by reference herein. These patents describe an apparatus comprising a piezoelectric actuating element coupled to a liquid atomization plate. The piezoelectric actuating element vibrates the liquid atomization plate in response to alternating electrical voltages applied to the actuating element. The vibration of the plate causes atomization of a liquid supplied to it by a liquid delivery system. An electrical circuit is provided to supply the alternating electrical voltages to conductive elements that are in electrical contact with opposite sides of the actuating element. The conductive elements may also serve to support the actuating element and the liquid atomization plate in a housing that contains the device.

SUMMARY OF THE INVENTION

According to one aspect of the present invention, a diffusion device comprises a bottom portion having a bottom cover disposed thereon. The device further includes a top portion having a top cover disposed atop the bottom portion and a pump assembly disposed between the top cover and the bottom cover. First, second, and third arm portions extend from the pump assembly, wherein the first, second, and third arm portions include first, second, and third piezoelectric devices, respectively, attached thereto.

According to yet another aspect of the present invention, a diffusion device comprises a top portion having a top cover and a bottom portion having a bottom cover, wherein the top cover is disposed atop the bottom cover, thereby forming a cavity therebetween. The device further includes a container disposed in the cavity, wherein the container includes an active material therein and a wick extending therefrom. Still further, the device includes a spring-loaded pump assembly slidingly connected to the bottom cover and including a piezoelectric element extending therefrom. When the top cover is inserted over the spring-loaded pump assembly, the pump assembly moves downwardly such that the piezoelectric element is moved into contact with the wick and when the cover is removed, the pump assembly moves upwardly and out of contact with the wick.

According to still a further aspect of the present invention, a method of diffusing first, second, and third active materials from a diffusion device comprises the step of selecting an intensity level for dispersion of the active material(s), wherein the intensity level is determined by the dwell time between active material emissions. The method further includes the step of selecting from one of the five different modes of operation including: emitting the first active material, emitting the second active material, emitting the third active material, alternating between emission of the first, second, and third active materials based on a first predetermined duration, and alternating between emission of the first, second, and third active materials based on a second predetermined duration.

Other aspects and advantages of the present invention will become apparent upon consideration of the following detailed description and the attached drawings, in which like elements are assigned like reference numerals.

BRIEF DESCRIPTION OF THE DRAWINGS

FIG. 8 is a top perspective view of a bottom portion of the diffusion device of FIG. 1;

FIG. 12 is a side elevation view of the diffusion device of FIG. 11;

FIG. 12A is a bottom perspective view of a top cover of the diffusion device of FIG. 10;

FIG. 25 is a flow diagram illustrating the logic associated with switches for controlling any of the diffusion devices of the present invention.

DETAILED DESCRIPTION OF THE PREFERRED EMBODIMENTS

Figure 1:
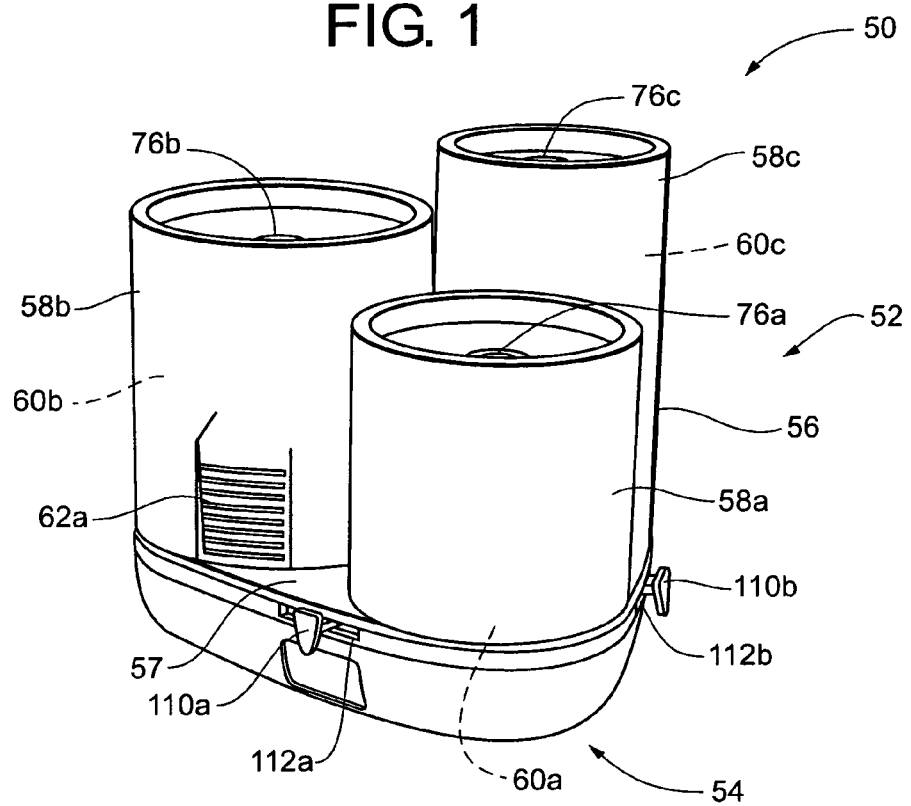
FIG. 1 is a top perspective view of a first embodiment of a diffusion device according to the present invention.

FIGS. 1-9C depict a first embodiment of a diffusion device 50 according to the present invention. As seen in FIG. 1, the diffusion device 50 includes a top portion 52 and a bottom portion 54. The top portion 52 includes a top cover 56 that may be removed from the bottom portion 54 in order to access contents of the diffusion device 50. A bottom cover 57 (FIG. 2) is disposed atop the bottom portion 54 to separate contents of the bottom portion 54 from contents of the top portion 52.

Figure 2:
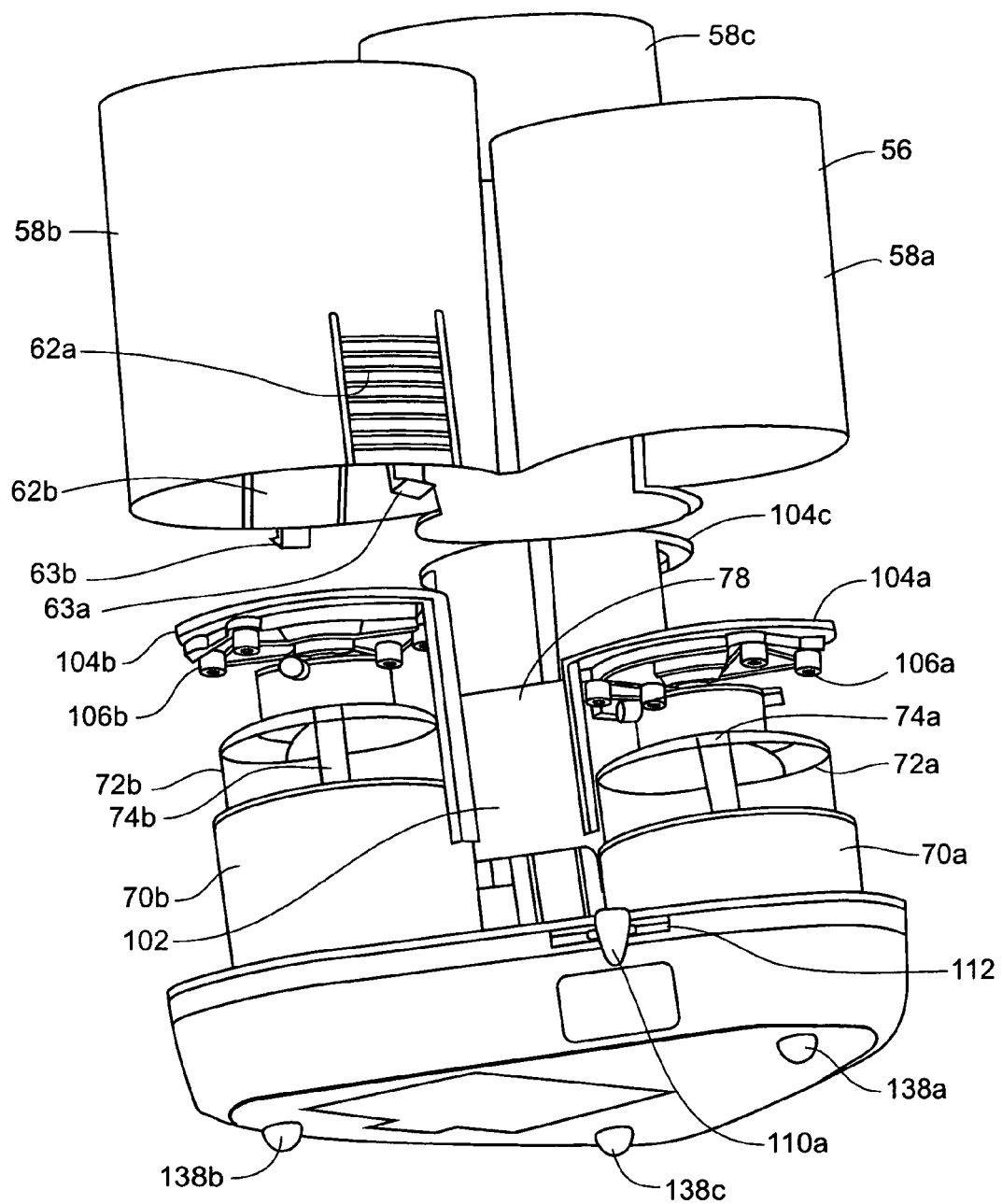
FIG. 2 is a bottom perspective view of the diffusion device of FIG. 1 illustrating a top cover partially removed therefrom.

The top cover 56 comprises first, second, and third columns 58a-58c that form first, second, and third compartments 60a-60c, respectively, between the top portion 52 and the bottom portion 54. As seen in FIG. 2, the second column 58b preferably includes first and second flexible portions 62a, 62b comprising flaps having first and second outwardly directed tabs 63a, 63b, respectively, extending therefrom. In a closed position, the tab 63a, 63b extend into interfering relationship with walls 64a, 64b defining apertures 65a, 65b (FIGS. 4 and 7, respectively) disposed in the bottom cover 57. When pressure is exerted on the flexible portions 62a, 62b toward one another, the tabs 63a, 63b moved out of interfering relationship with the walls 64a, 64b defining the apertures 65a, 65b, thereby permitting the top cover 56 to be removed from the bottom portion 54.

Figure 3:
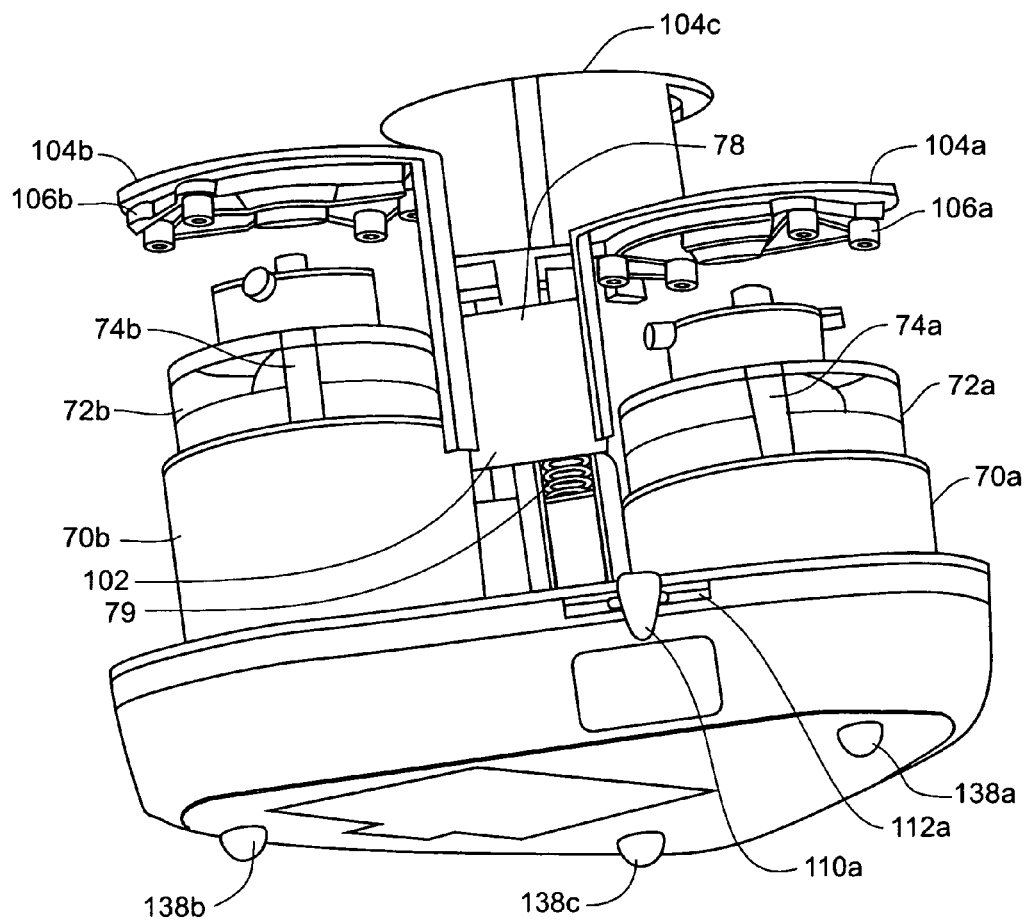
FIG. 3 is a bottom perspective view of the diffusion device of FIG. 1 illustrating the top cover fully removed therefrom.
Figure 4:
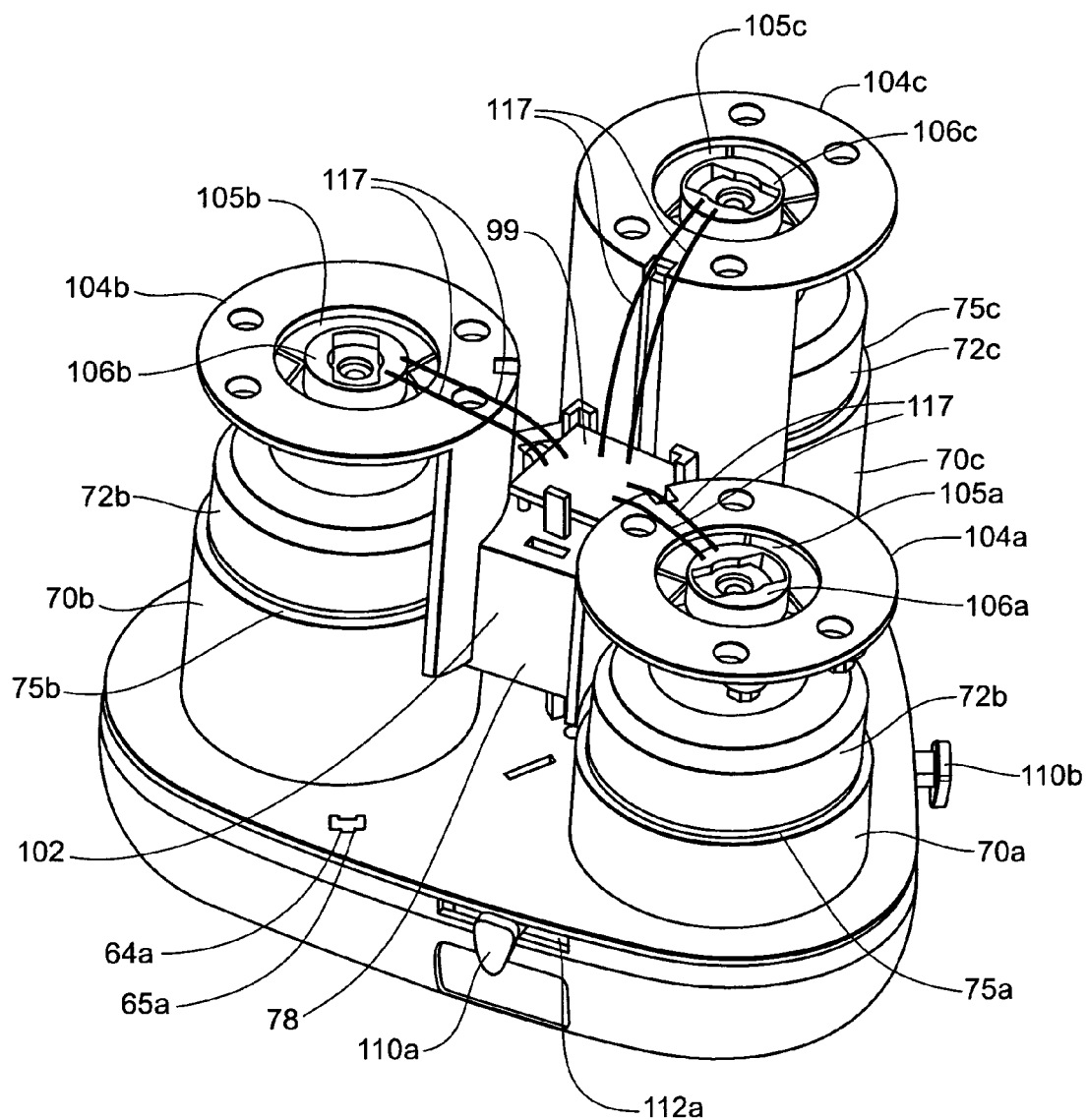
FIG. 4 is a top perspective view of the diffusion device of FIG. 3.

As seen in FIGS. 2-4, the top portion 52 includes first, second, and third pedestals 70a-70c for holding first, second, and third containers 72a-72c, respectively, wherein each of the containers 72a-72c includes an active material therein. The pedestals 70a-70c are preferably, although not necessarily, integral with and extend upwardly from the bottom cover 57. Each of the containers 72a-72c includes a wick 74a-74c, respectively, in communication with the active fluid therein and extending through a top portion thereof. Each of the pedestals 70a-70c includes an annular outer lip 75a-75c, respectively, that positions the respective container 72a-72c on the respective pedestal 70a-70c. The pedestals 70a-70c in this embodiment only differ from one another in that the pedestals 70a-70c have different heights. The first pedestal 70a is disposed at a first height, the second pedestal 70b is disposed at a second height that is greater than the first height, and the third pedestal 70c is disposed at a third height that is greater than the first and second heights. Optionally, some or all of the pedestals 70a-70c may be disposed at the same height.

Figure 5:
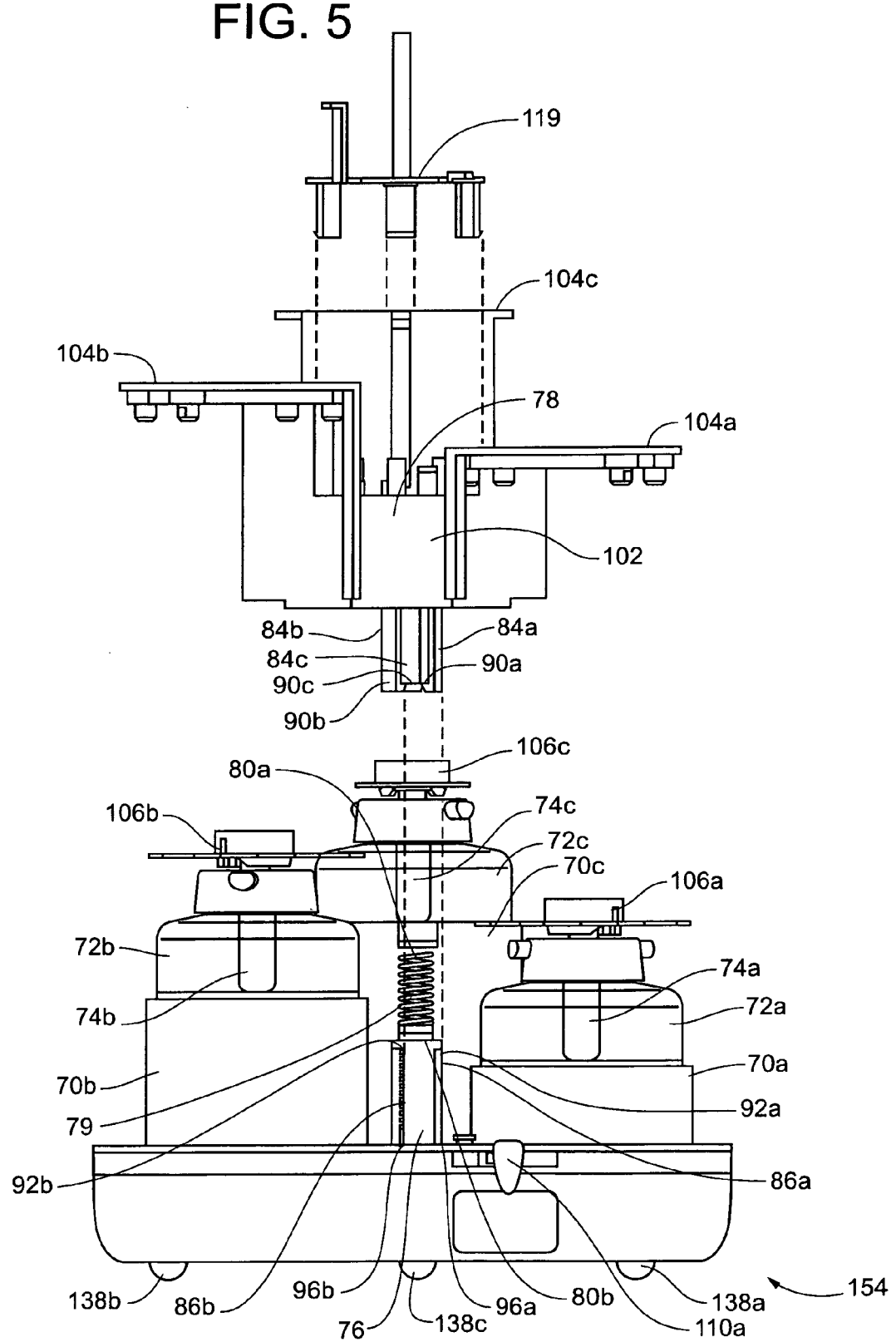
FIG. 5 is an exploded view of the diffusion device of FIG. 3.
Figure 6:
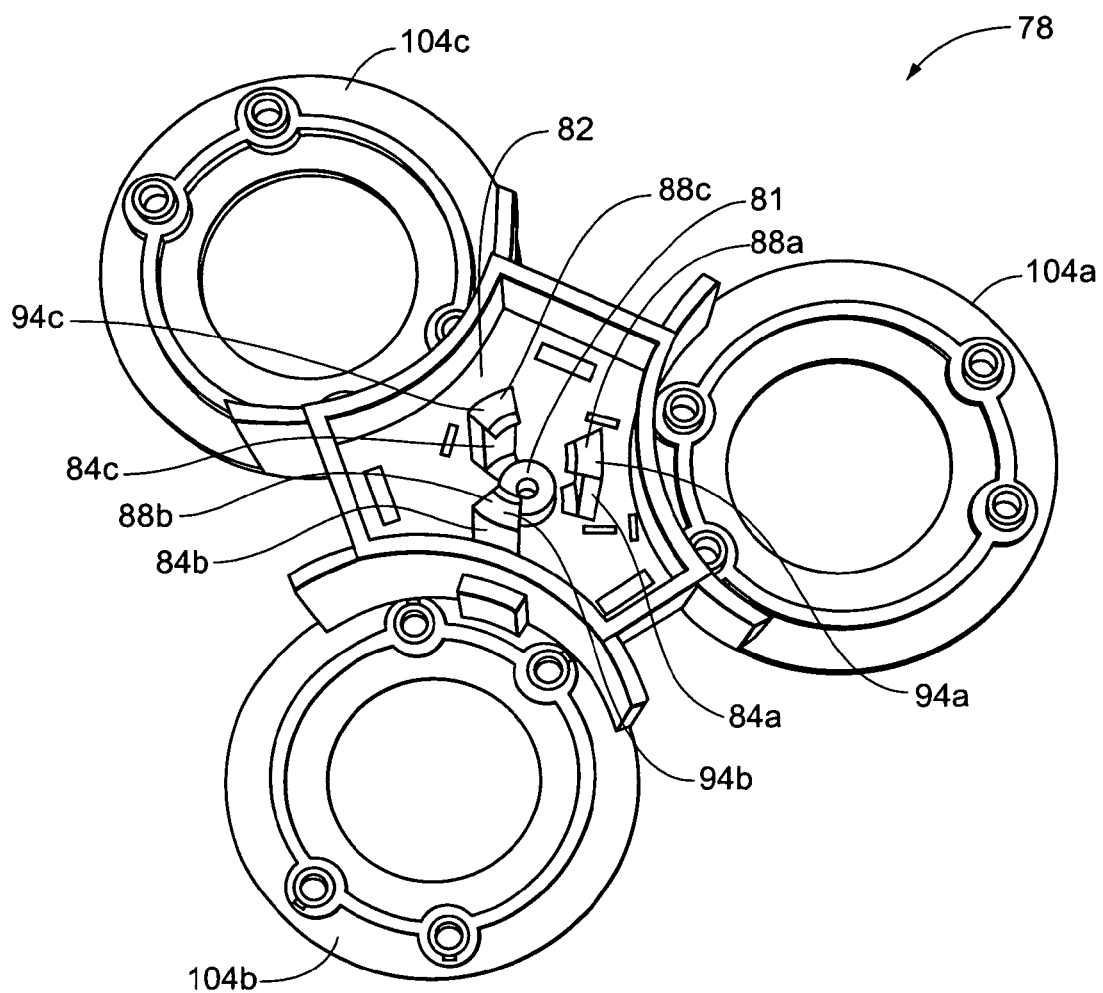
FIG. 6 is a bottom perspective view of a pump assembly of the diffusion device of FIG. 1.
Figure 7:
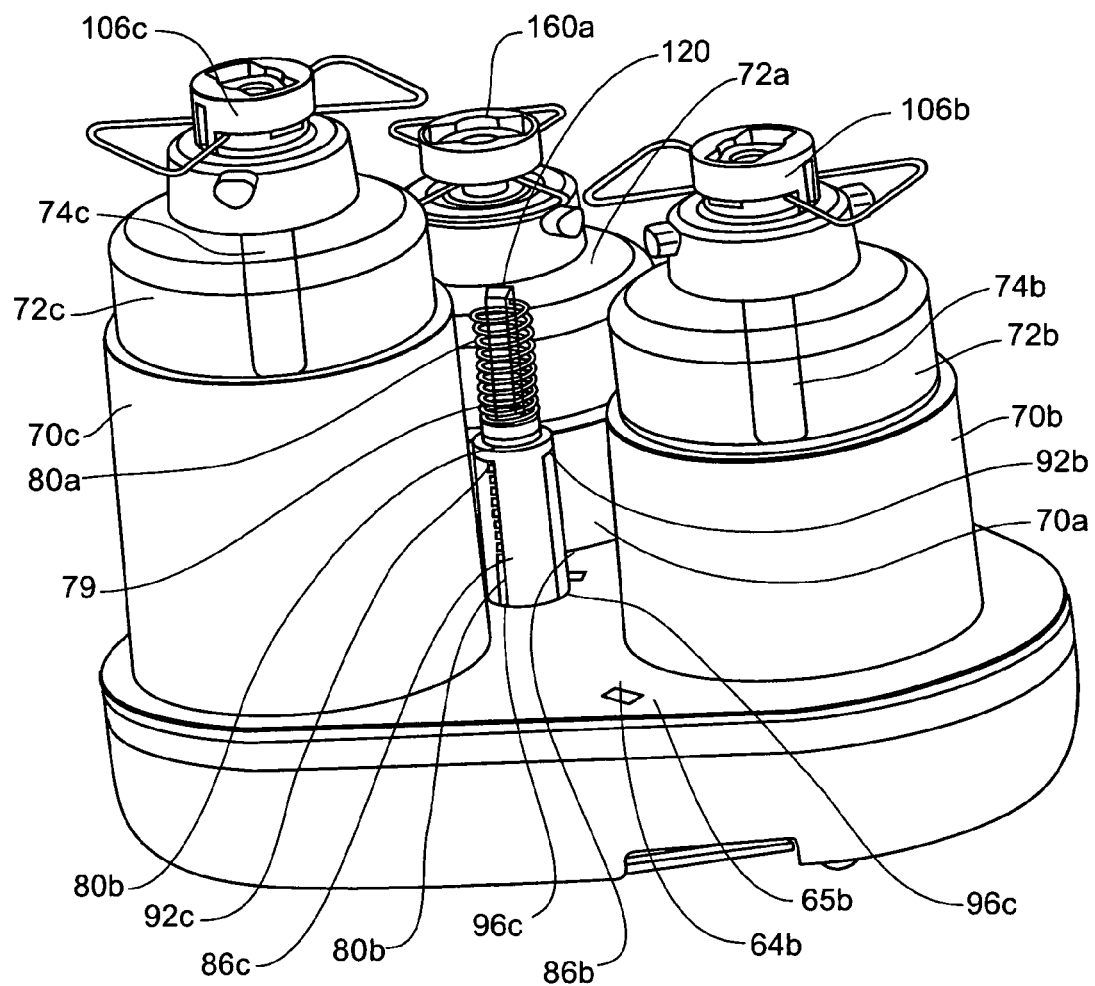
FIG. 7 is top perspective view of the diffusion device of FIG. 3.

Referring to FIGS. 5-7, the top portion 52 further includes a central cylindrical support 76 (visible in FIGS. 5 and 7) integral with and extending upwardly perpendicularly from the bottom cover 57. Optionally, the support 76 and the bottom cover 57 may not be integral and may, instead, be attached together in any manner known in the art. A pump assembly 78 is slidingly disposed over a top portion of the support 76 and a spring 80 is disposed between the support 76 and the pump assembly 78. The spring 79 has a first end 80a that surrounds a cylindrical boss 81 disposed on an underside 82 of the pump assembly 78. The spring 79 extends to and through the support 76 such that a second end 80b of the spring 79 abuts the bottom cover 57. The spring 79 biases the pump assembly 78 upwardly.

As further seen in FIGS. 5-7, three downwardly depending posts 84a-84c surround the support 76 and the spring 80 and are located in register with three longitudinal slots 86a-86c, respectively, in the support 76. The posts 84a-84c include inwardly-directed flanges 88a-88c, respectively, that extend into and through the slots 86a-86c, respectively. The slots 86a-86c are equally spaced about a circumference of the support 76. The posts 84a-84c and flanges 88a-88c guide the movement of the pump assembly 78. Specifically, the posts 84a-84c and flanges 88a-88c allow linear up and down travel against the biasing of the spring 80 between an upper limit defined as a point where upper surfaces 80a-80c of the flanges 88a-88c contact upper walls 92a-92c in part defining the slots 86a-86c and a lower limit defined as a point where lower surfaces 94a-94c of the flanges 88a-88c contact lower walls 96a-96c in part defining the slots 86a-86c. The slots 86a-86c capture the flanges 88a-88c extending from the respective posts 84a-84c so as to maintain the angular alignment of the piezoelectric devices 86a-86c relative to the pedestals 70a-70c and, therefore, the containers 72a-72c.

Referring now to FIGS. 2-4, the pump assembly 78 includes a central portion 102 and first, second, and third arm portions 104a-104c extending from and integral with the central portion 102, wherein each of the arm portions 104a-104c includes an aperture 105a-105c therein (FIG. 4). Each of the arm portions 104a-104c also includes a piezoelectric pump or device 106a-106c attached to an underside thereof, such that the piezoelectric devices 106a-106c are disposed below and in alignment with the respective apertures 105a-105c.

Any of the piezoelectric devices described in any of the patents incorporated by reference herein may be utilized for the piezoelectric devices 106a-106c. In general, these devices apply an alternating voltage to a piezoelectric element to cause the element to expand and contract. The piezoelectric element is coupled to a perforated orifice plate, which in turn is in surface tension contact with a liquid source. The expansion and contraction of the piezoelectric element causes the orifice plate to vibrate up and down whereupon liquid is driven through the perforations in the orifice plate and is then emitted upwardly in the form of aerosolized particles.

When the top cover 56 is disposed atop the bottom portion 54, the pedestals 70a-70c, the containers 72a-72c, the arm portions 104a-104c, and the piezoelectric devices 106a-106c reside within the compartments 60a-60c, respectively. When in this closed position, top portions 108a-108c of the columns 58a-58c, respectively, force the arm portions 104a-104c downwardly, thereby forcing the piezoelectric devices 106a-106c into contact with the wicks 74a-74c, respectively. When the top cover 56 is removed, the pump assembly 78 as a whole moves upwardly in response to the biasing provided by the spring 79, thereby causing the arm portions 104a-104c to move upwardly and moving the piezoelectric devices 106a-106c out of contact with the respective wicks 74a-74c. Without contact of the piezoelectric devices 106a-106c with the wicks 74a-74c, respectively, the piezoelectric devices 106a-106c cannot properly atomize the active materials contained within the respective containers 72a-72c.

First, second, and third circular apertures 76a-76c are disposed in top portions of the first, second, and third columns 58a-58c, respectively, as seen in FIG. 1. When the top cover 56 is disposed atop the bottom portion 54, the apertures 76a-76c are aligned with the respective apertures 105a-105b in the arm portions 104a-104c, and thus are aligned with the respective piezoelectric device 106a-106c. The circular apertures 76a-76c in the columns 58a-58c provide an outlet for active materials that are atomized by the piezoelectric devices 106a-106c.

As best seen in FIGS. 1 and 4, an operating mode actuating arm 10a and an emission frequency actuating arm 110b both in the form of pivoting arms extend from the bottom portion 54 of the diffusion device 50. Specifically, the operating mode actuating arm 110a controls the operating mode of diffusion device 50 and extends through an aperture 92a in the bottom portion 54 of the device 50. The emission frequency actuating arm 110b controls the emission frequency of the diffusion device 50 and extends through another aperture 112 in the bottom portion of the device 50.

FIG. 8 depicts the bottom portion 54 of the diffusion device 50 with the bottom cover 57 removed therefrom. The bottom portion 54 includes the operating mode actuating arm 110a and the emission frequency actuating arm 110b both operatively connected to first and second slide switches 114a, 114b, respectively (discussed in more detail hereinafter). The slide switches 114a, 114b are also operatively connected to a printed circuit board (PCB) 116 for controlling the operating mode and emission frequency of the piezoelectric devices 106a-106c.

Each of the selectors 110a, 110b includes five selectable positions. Selection of a position by the user with respect to one or both of the selectors 110a, 110b indicates to the respective slide switch 114a, 114b the current position of the respective selector 110a, 110b. The positions of the slide switches 114a, 114b are detected by the PCB 116. Components mounted on the PCB 116 control the piezoelectric devices 106a-106c corresponding to the positions of the selectors 110a, 110b. As seen in FIG. 4, two wires 117 extend from each of the piezoelectric devices 106a-106c to a jumper board 119, wherein the jumper board 119 is connected to the PCB 116 by a ribbon cable 120, which runs through a center of the spring 79. The flexible ribbon cable 120 must be flexible and must provide sufficient slack to accommodate the up and down movement of the pump assembly 78 as previously described.

In the present invention, every single emission or spray of active material has a period which includes an on time or period and a dwell time or period. The on time represents a time period for which an active material is actually emitted and the dwell time represents a duration between sprays in which the diffusion device 50 is inactive, i.e., not emitting an active material therefrom. Additionally, any of the active materials may be actuated for a predetermined duration, wherein the predetermined duration represents the entire length of time which an active material is to be emitted intermittently by the device. Preferably, a predetermined duration includes multiple periods as described above, but optionally may only includes a single period.

The operating mode selector 110a controls the mode of operation of the diffusion device 50. For example, in one embodiment, the operating mode selector 110a may include a slide switch with five different positions. When a user moves the selector 110a to a first position, a mode of operation may be initiated wherein the first active material from the first container 72a is emitted intermittently. Preferably, although not necessarily, emissions or sprays occur on a periodic basis, wherein the dwell time between sprays is constant for a selected intensity (as described in greater detail hereinafter). When the user slides the selector 110a to a second position, a first auto mode of operation may be initiated wherein the diffusion device 50 alternates between emitting the active materials of the first, second, and/or third containers 72a-72c. In this mode, the sprays are preferably, although not necessarily, intermittent as described above with respect to the first mode. Illustratively, in one embodiment, the active material from one of the containers 72a-72c is sprayed intermittently for a first predetermined duration, thereafter the active material from a second of the containers 72a-72c is sprayed intermittently for a second predetermined duration, and thereafter the active material from a third of the containers 72a-72c is sprayed intermittently for a third predetermined duration. Any or all of the first, second, and third predetermined durations be the same, or the predetermined durations may all be different. The predetermined durations may be any preferred periods of time, but preferably are between about one minute and about twenty-four hours. Preferably, the predetermined period is between about 3 hours and about 24 hours. In one preferred embodiment, the predetermined period is about 3 hours and in another preferred embodiment, the predetermined period is about 24 hours. Other optional modes of operation for the first auto mode will be described hereinafter.

When the selector 10a is moved to a third position, a mode of operation may be entered wherein the second active material from the second container 72b is emitted intermittently, as described in detail above. In a fourth position, a second auto mode of operation may be initiated wherein the diffusion device 50 alternates between emitting the active materials from the first, second, and/or third active containers 72a-72c. The second auto mode may be similar to the auto mode described hereinabove with respect to the first auto mode, or may be any alternating mode of operation as described in detail hereinbelow. When the selector 110a is moved to a fifth position, a mode of operation may be entered wherein the third active material from the third container 72c is emitted intermittently, as described in detail above. Optionally, any of such described modes of operation may be placed in any position.

Although only two auto modes are described in the previous example, any number of auto modes can be utilized wherein no auto modes or used or up to five auto modes are used, wherein the auto modes are the same or different.

Various different auto modes may be incorporated into any of the embodiments herein. Such additional and/or substitute modes of operation may be utilized with changes to the circuitry, described hereinafter, and/or additional circuitry. Optionally, in one exemplary auto mode, the auto mode may function similar to the first auto mode discussed hereinabove, wherein such a sequence of active material emission may occur only once or may be repeated continuously. Still optionally, any two of the active materials may be emitted in an alternating fashion, as described above. Although the predetermined durations contemplate multiple periods for an active material, it is possible to utilize only one period, thus one spray, for one or more active materials.

Although the embodiments discussed thus far contemplate sequencing of the active materials, the first, second, and/or third active materials may be randomly actuated. In such a random mode, the on times, the dwell times, and/or the predetermined durations for each of the emitted active materials may all be the same or may all be different.

Illustratively, another mode varies the on time of one or more active material(s) that are emitted from the diffusion device 50. For example, the on time may be varied by gradually increasing or decreasing the time in which an active material is sprayed by the device. Optionally, another mode varies the dwell time for one or more active material(s) by gradually increasing or decreasing the time between sprays of active material.

In yet another mode of operation, the on time for an active material may be increased to thereby release more active material and may remain at that on time for a predetermined duration. The predetermined duration may be any time limit that prevents habituation of the active material, such as any time period between one minute and thirty minutes. After the predetermined duration, the on time for the active material may be decreased to thereby release less active material and may remain at that on time for the same or a different predetermined duration. This cycle may be repeated or may be repeated in a random or complex pattern. Also, any number of different active material emission levels may be utilized in such a mode of operation. Optionally, the dwell time for an active material may be decreased to thereby spray active material more frequently and may remain at that dwell time for a predetermined duration. Once the predetermined duration has expired, the dwell time may be increased to thereby spray active material less frequently and may remain at such dwell time for the same or different predetermined duration. Still optionally, the on time and dwell time for one or more active material may be decreased and/or increased as described above.

In another mode of operation, emission of all active materials may be discontinued for a predetermined off time, wherein the off time is a time period in which an active material is discontinued. The predetermined off time may be any period of time that allows the active material level to decrease or partially or fully dissipate from the surrounding environment, but preferably the predetermined off time is between about one minute and about thirty minutes. After the predetermined off time has expired, the emission of active material is resumed. This cycle may be repeated with the same, increasing, or decreasing off times.

Still alternatively, in another mode of operation, two or more active materials may be dispensed simultaneously in any manner as discussed herein.

Any of the modes of operation as disclosed herein or as known in the art may be utilized alone or in any combination. Also, any of these modes of operation may be utilized with a diffusion device that emits a single active material or a diffusion device that emits multiple active materials.

The emission frequency selector 110b controls the frequency of active material emission of the diffusion device 50. For example, in one embodiment, the selector 10b may include a slide switch with five different positions. Each spray of fragrance includes an on-time and a dwell time, wherein the on-time represents the time period in which a fragrance is sprayed and the dwell time represents a duration between sprays in which the diffusion device 50 is inactive, i.e., not emitting active material. Preferably, although not necessarily, the on-time remains constant. Optionally, the on-time may be of variable duration.

A first position of the selector 110b may actuate a first dwell time, a second position may actuate a second dwell time, and a third position may actuate a third dwell time. Still further, fourth and fifth positions may actuate fourth and fifth dwell times, respectively. The dwell times may be of preferred durations, but preferably are between a few seconds and a few minutes. Most preferably, the first, second, third, fourth, and fifth dwell times are 30 seconds, 21 seconds, 15 seconds, 9 seconds, and 4.5 seconds, respectively. Another optional combination includes dwell times of 27 seconds, 18 seconds, 12 seconds, 9 seconds, and 4.5 seconds. Still another combination includes dwell times of 18 seconds, 12 seconds, 9 seconds, 6 seconds, and 4.5 seconds.

Optionally, the selectors 110a and 110b may include any number of positions corresponding to a preferred number of modes or intensities. Also, the positions may correspond to any mode or intensity.

As further seen in FIGS. 8 and 9A-C, the bottom portion 54 of the diffusion device 50 includes two batteries 122a, 122b that preferably provide direct current that is converted into high-frequency alternating current power that is selectively applied to the piezoelectric devices 106a-106c. Optionally, the diffusion device 50 may be powered by alternating household current, which is rectified and converted to high-frequency alternating current power that is intermittently applied to the piezoelectric devices 106a-106c. The batteries 122a, 122b may be any conventional dry cell battery such as "A", "AA", "AAA", "C", and "D" cells, button cells, watch batteries, and solar cells, but preferably, the batteries 98a, 98b are "AA" or "AAA" cell batteries. Although two batteries are preferred, any number of batteries that would suitably fit within the device and provide adequate power level and service life may be utilized.

Figure 9A:
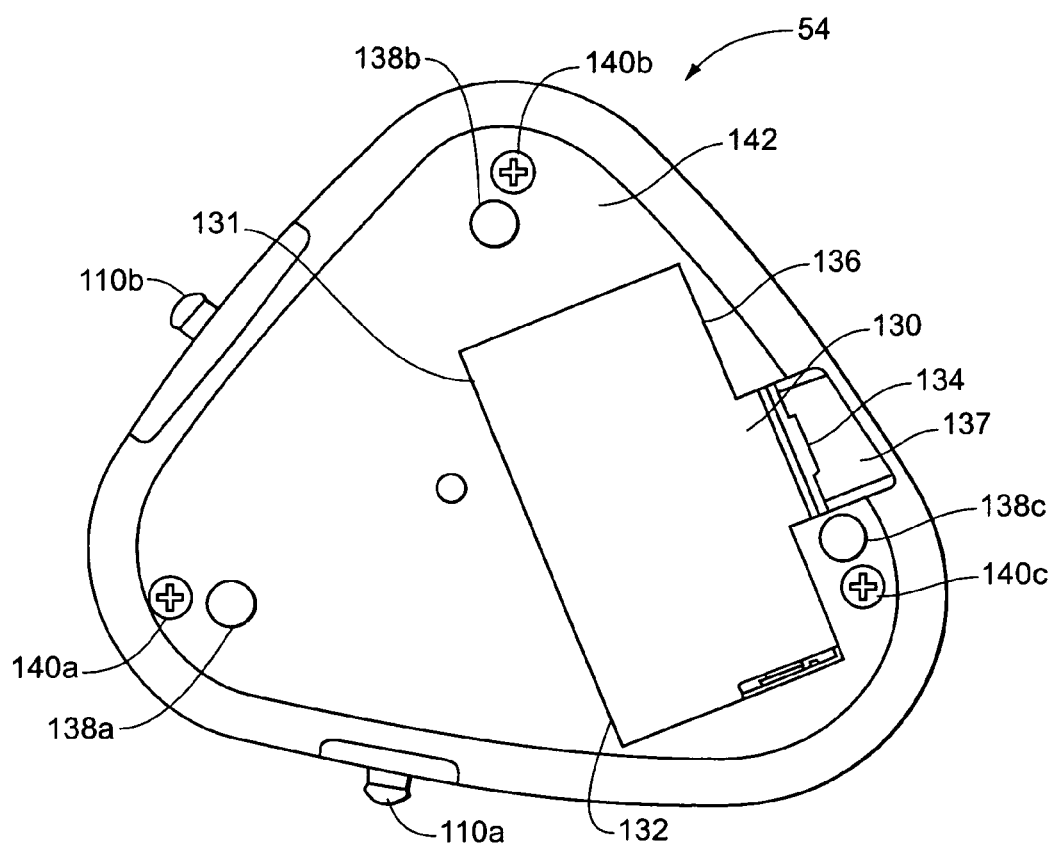
FIG. 9A is a bottom elevational view of the diffusion device of FIG. 1.

Referring to FIG. 9A, the bottom portion 54 includes a battery door 130 that includes a hinge 131 at a first end 132 thereof and a latching mechanism 134 at a second end 136 thereof. The latching mechanism 134 interacts with a locking recess 136 in the bottom portion 54 for holding the battery door 130 in a closed position. The latching mechanism 134 may be flexed to release the latching mechanism 134 from the locking recess 136, such that the battery door 130 may pivot about the hinge 131 to open the battery door 130 and allow access to the bottom portion 54.

Figure 9B:
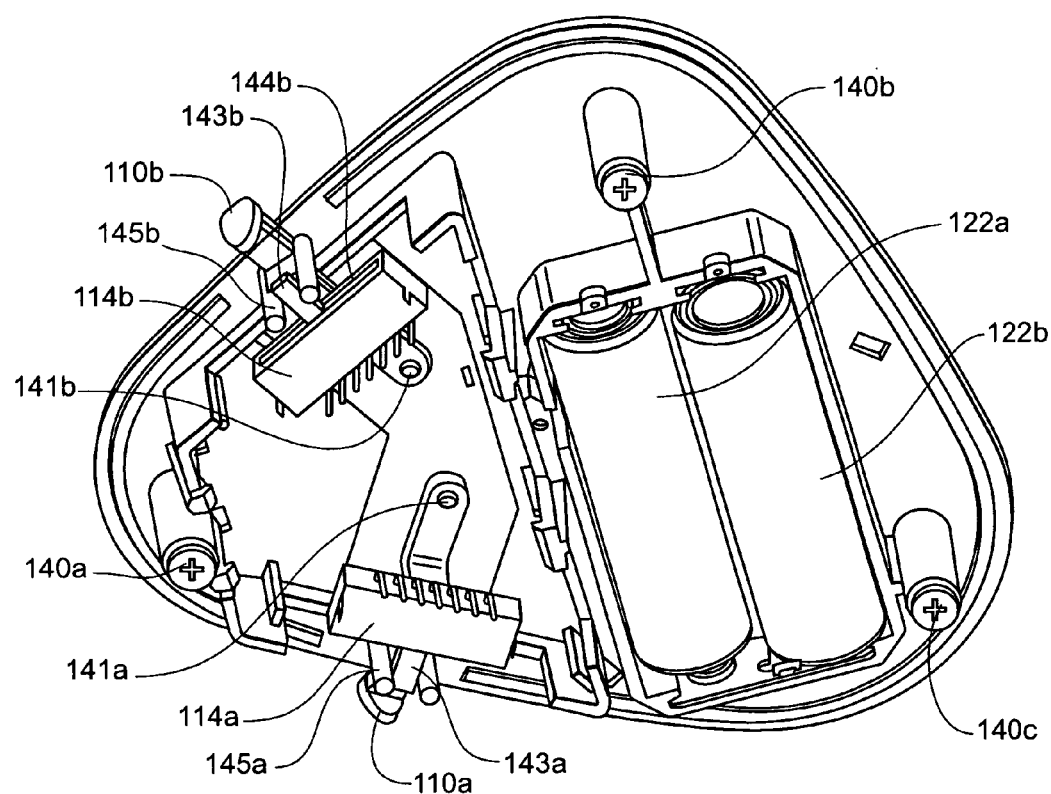
FIGS. 9B and 9C are bottom perspective views of the diffusion device of FIG. 9A illustrating a bottom portion removed therefrom.
Figure 9C:
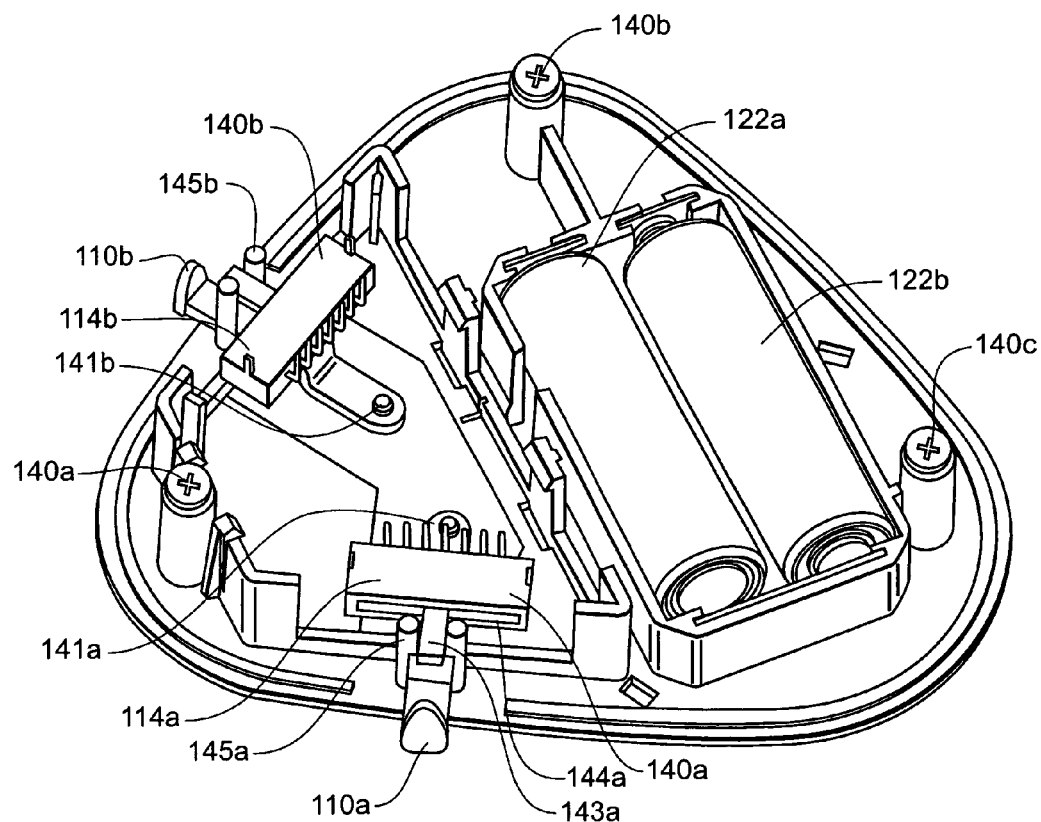

As seen in FIGS. 9B and 9C, two pins 141a, 141b extend from a bottom surface 142 of the bottom cover 57, wherein the pins 141a, 141b provide a pivot point to the selectors 110a, 110b, respectively. Each of the slide switches 114a, 114b includes a button 143a, 143 extending therefrom and a slot 144a, 144b therein, wherein the buttons 143a, 143 are movable along the respective slot 144a, 144b to one of five detent positions. A yoke 145a, 145b extending from each of the selectors 110a, 110b, respectively, surrounds the respective button 143a, 143b on sides thereof to move the button 143a, 143b along the respective slot 144a, 144b.

The bottom portion 54 may further include optional feet 138a-138c extending therefrom to aid in stabilizing the diffusion device 50. Although three feet 138 are depicted, any suitable number of feet 138 for stabilizing the diffusion device 50 may be utilized.

As further seen in FIGS. 9A-C, first, second, and third screws 140a-140c are disposed in a bottom surface 142 of the bottom portion 54. The screws 140a-140c extend through the bottom portion 54 to connect the bottom portion 54 to the bottom cover 57. Optionally, the bottom portion 54 may be attached to the bottom cover 57 by heat-staking or any other suitable fastening means, including, for example, rivets, press fit, snap fit, ultrasonic welding, adhesives, or the like and combinations thereof.

Figure 10:
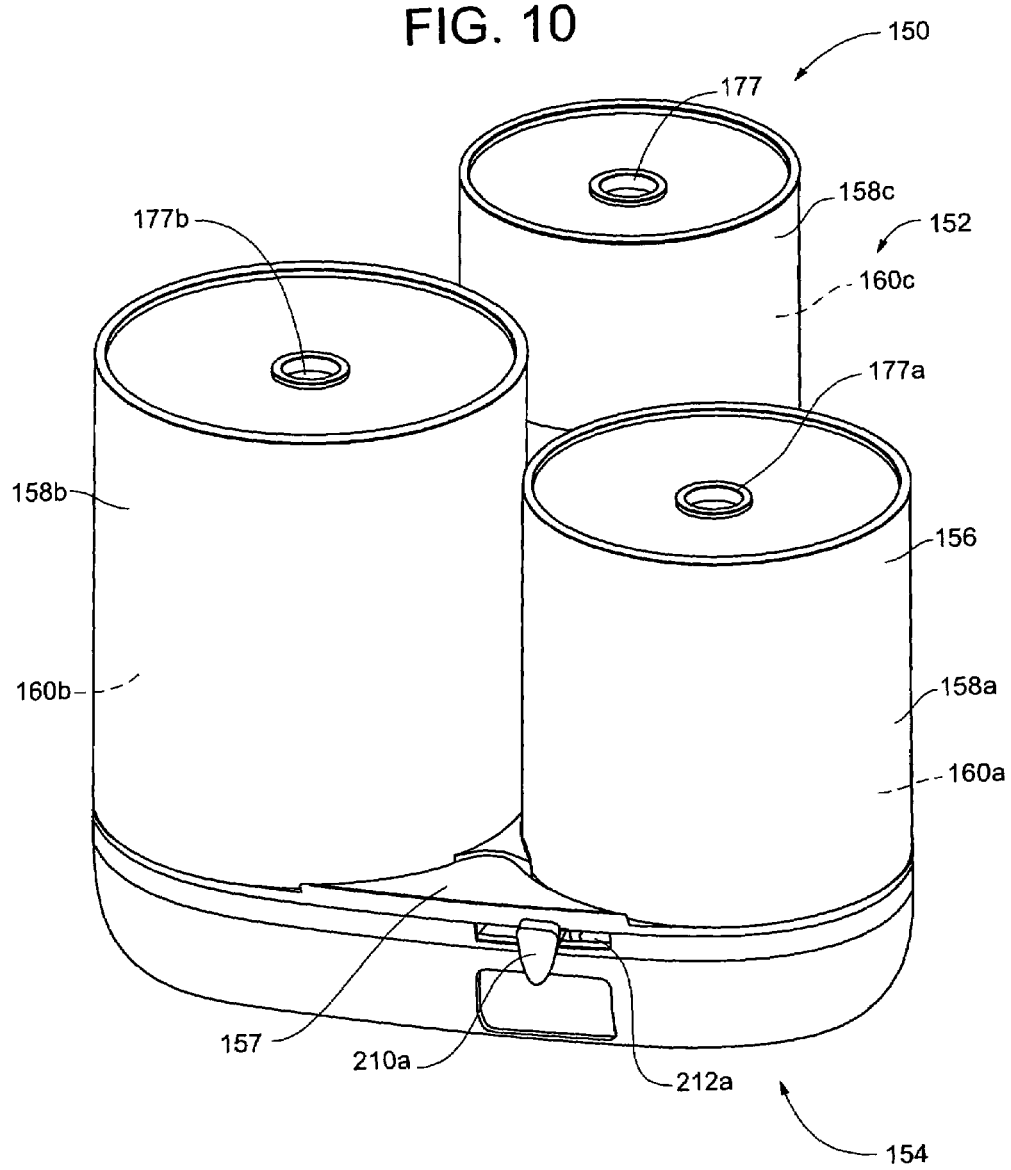
FIG. 10 is a top perspective view of a second embodiment of a diffusion device according to the present invention.
Figure 11:
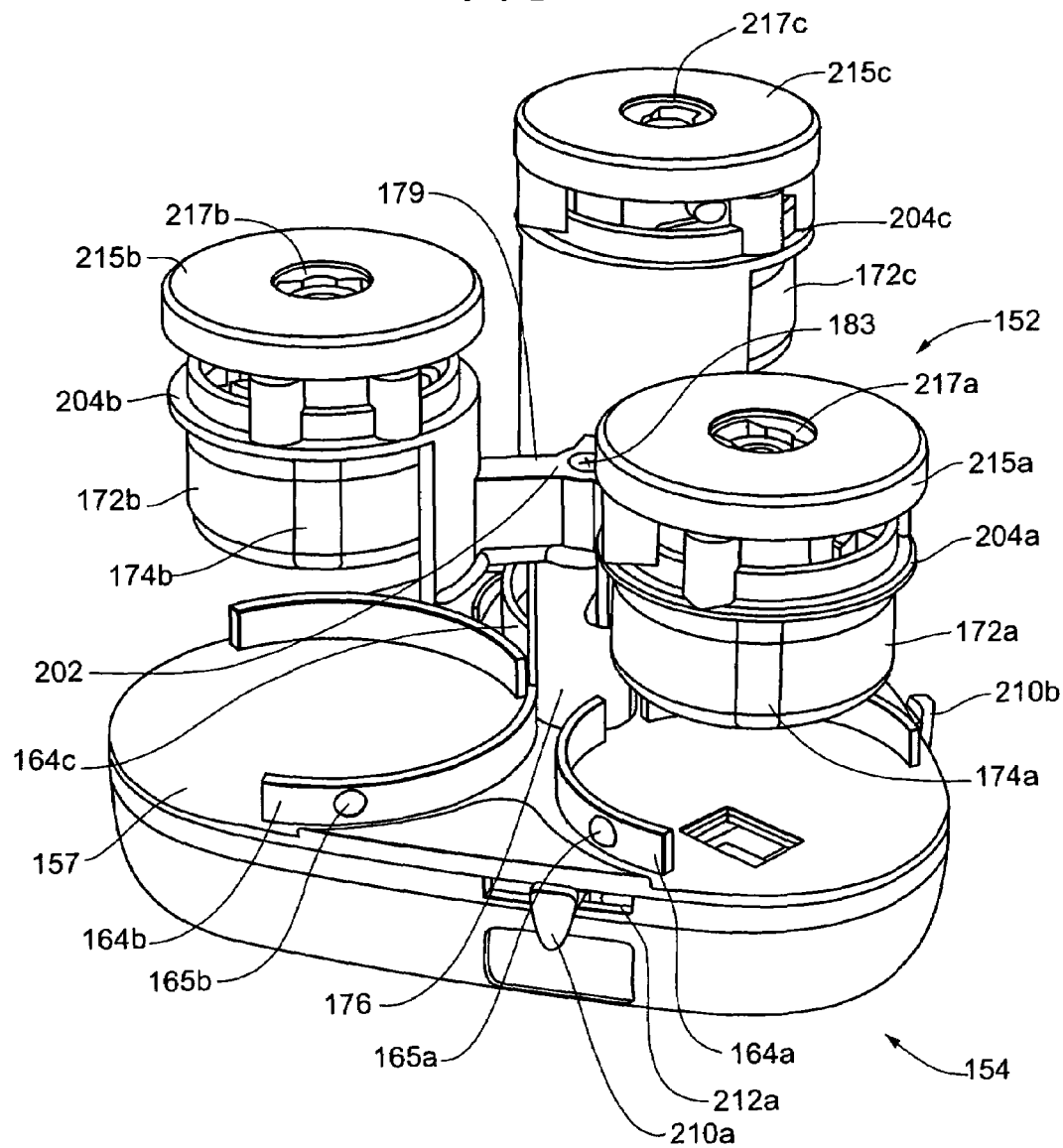
FIG. 11 is a top perspective view of the diffusion device of FIG. 10 illustrating a top cover removed therefrom.
Figure 13:
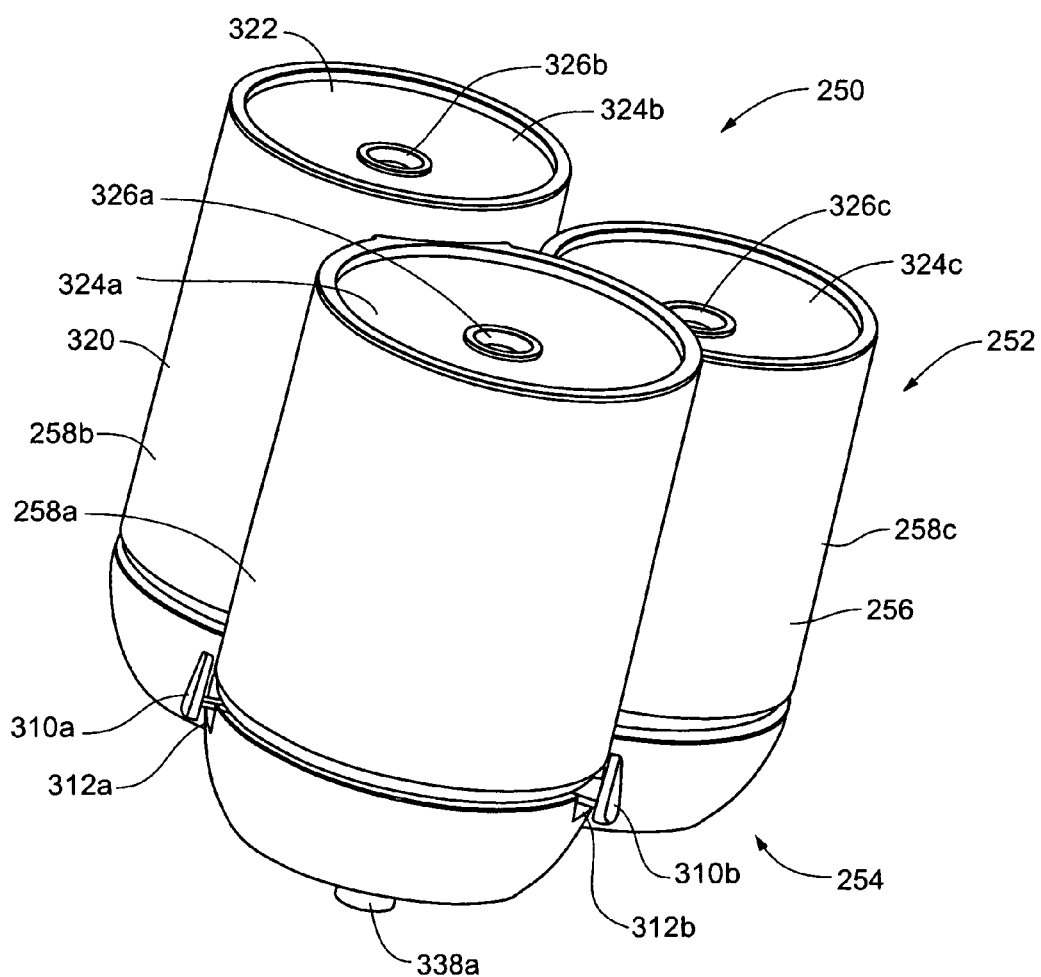
FIG. 13 is a top perspective view of a third embodiment of a diffusion device according to the present invention.

A second embodiment of a diffusion device 150 of the present invention is depicted in FIGS. 10-12. Similar to the embodiment of FIGS. 1-9, the diffusion device 150 includes a top portion 152 and a bottom portion 154. The top portion 152 includes a top cover 156 that may be removed from the bottom portion 154 in order to access contents of the diffusion device 150. A bottom cover 157 is disposed over the bottom portion 154 in order to separate contents of the bottom portion 154 from contents of the top portion 152.

The top cover 156 comprises first, second, and third cylindrical columns 158a-158c that form first, second, and third compartments 160a-160c, respectively between the top portion 152 and the bottom portion 154. Preferably, as seen in FIG. 12A, inner surfaces 161a-161c of each of the cylindrical columns 158a-158c include two opposing depressions 163a-163c. Further, as seen in FIGS. 11 and 12, the bottom cover 157 includes three semi-circular projections 164a-164c integral therewith and extending upwardly therefrom, wherein each of the projections 164a-164c includes two notches 165a-165c disposed thereon. When the top cover 156 is inserted atop the bottom cover 157, the notches 165a-165c engage walls forming the depressions 163a-163c to retain the top cover 156 on the bottom cover 157.

As seen in FIGS. 11 and 12, the top portion 152 includes a support 176 integral with and extending perpendicularly from the bottom cover 157. Optionally, the support 176 and the bottom cover 157 may not be integral and may, instead, be attached together in any manner known in the art. A stationary pump assembly 179 is secured to the support 176 by a screw 183, but optionally may be secured by any known fastening means.

Referring to FIGS. 10 and 11, the pump assembly 179 includes a central portion 202 having first, second, and third arm portions 204a-204c extend from and integral with the central portion 202, wherein each of the arm portions 204a-204c includes a piezoelectric device 206a-206c respectively attached to a top portion thereof. Retainer caps 215a-215c (FIG. 11) having circular apertures 217a-217c, respectively, therein are disposed above the arm portions 204a-204c atop the piezoelectric devices 206a-206c. The piezoelectric devices 206a-206c operate in the same manner as the piezoelectric devices 106a-106c described in connection with the embodiment of FIGS. 1-9.

Three containers 172a-172c each include a wick 174a-174c extending therefrom and a cap portion 207a-207c having two opposing connecting lugs 209a-209f extending therefrom. Further, each of the arm portions 204a-204c includes two opposing bayonet slots that accept the respective connecting lugs 209a-209f therein to allow the containers to be screwed into and retained in the corresponding arm portions 204a-204c. Such a connection is described in detail in Schramm et al. U.S. Pat. No. 6,446,880, which is assigned to the assignee of the present application and which is hereby incorporated by reference. Optionally, any other means for releasably connecting the containers 172a-172c with the arm portions 204a-204c may be utilized.

First, second, and third circular apertures 177a-177c are disposed in top portions 211a-211c of the first, second, and third columns 158a-158c, respectively, as seen in FIG. 10. When the top cover 156 is disposed atop the bottom portion 154, the containers 172a-172c, the arm portions 204a-204c, the piezoelectric devices 206a-206c, and the retainer caps 215a-215c reside within the compartments 160a-160c, respectively. The apertures 176a-176c in the columns 158a-158c, respectively, are aligned with the respective apertures 217a-217c in the retainer caps 215a-215c, and thus are aligned with the respective piezoelectric device 206a-206c. The circular apertures 176a-176c in the columns 158a-158c therefore provide an outlet for active materials that are atomized by the piezoelectric devices 206a-206c.

As best seen in FIGS. 11 and 12, an operating mode selector 210a and an emission frequency selector 210b both in the form of pivoting arms, extend from the bottom portion 154 of the diffuser 150. The operating mode selector 210a controls the mode of diffusion of device 150 and extends through an aperture 212a in the bottom portion 154 of the diffuser 150. The operating mode selector 210a is similar to and works similarly to the operating mode selector 110a of the embodiment of FIGS. 1-9. The emission frequency selector 210b controls the emission frequency of the diffusion device 150 and extends through another aperture 212b in the bottom portion 154 of the device 150. The emission frequency selector 210b is similar to and works similarly to the emission frequency selector 110b of the embodiment of FIGS. 1-9.

The bottom portion 154 contains the same components as shown and described in connection with the embodiment of FIGS. 1-9, and more specifically as seen in FIGS. 8 and 6. Although the embodiment of FIGS. 10-12 is show without feet, any number of feet may be utilized for stabilization of the device 150.

Although not seen in the embodiment of FIGS. 10-12, there is wiring that extends from each of the piezoelectric devices 206*a*-206*c* to the electrical components of the device 150. This wiring is preferably disposed on an underside of the retainer caps 215*a*-215*c* and would extend along the pump assembly 179, along the support, and through apertures in the bottom cover 157 into the bottom portion 154 of the device 150.

FIGS. 13-16 depict a third embodiment of a diffusion device 250 of the present invention that is similar to the embodiment of FIGS. 10-12. The diffusion device 250 includes a top portion 252 and a bottom portion 254. The top portion 252 includes a top cover 256 having a first integral portion 320 disposed atop the bottom portion 254, wherein the first integral portion 320 includes first, second, and third hollow columns 258*a*-258*c*. The top portion 252 further includes a second integral portion 322 (FIG. 14) that includes first, second, and third cover portions 324*a*-324*c* having apertures 326*a*-326*c*, respectively, through a center portion thereof. The first integral portion 320 and the second integral portion 322 provide an aesthetic advantage in that the first and second integral portions 322, 324 may have different colors, textures, and/or other features. For example, the first integral portion 320 may be opaque or translucent and the second integral portion 322 may be tinted a certain color. Further, the second integral portion 322 protects the piezoelectric devices 206*a*-206*c* and/or any wiring leading to the piezoelectric devices 206*a*-206*c*. As seen in FIGS. 13-16, the first integral portion 320 may be removed from the bottom portion 254 and the second integral portion 322 may also be removed, thereby exposing contents of the top portion 252 of the diffusion device 250. A bottom cover 257 (FIG. 14) is disposed over the bottom portion 254 in order to separate contents of the bottom portion 254 from the contents of the top portion 252.

Figure 14:
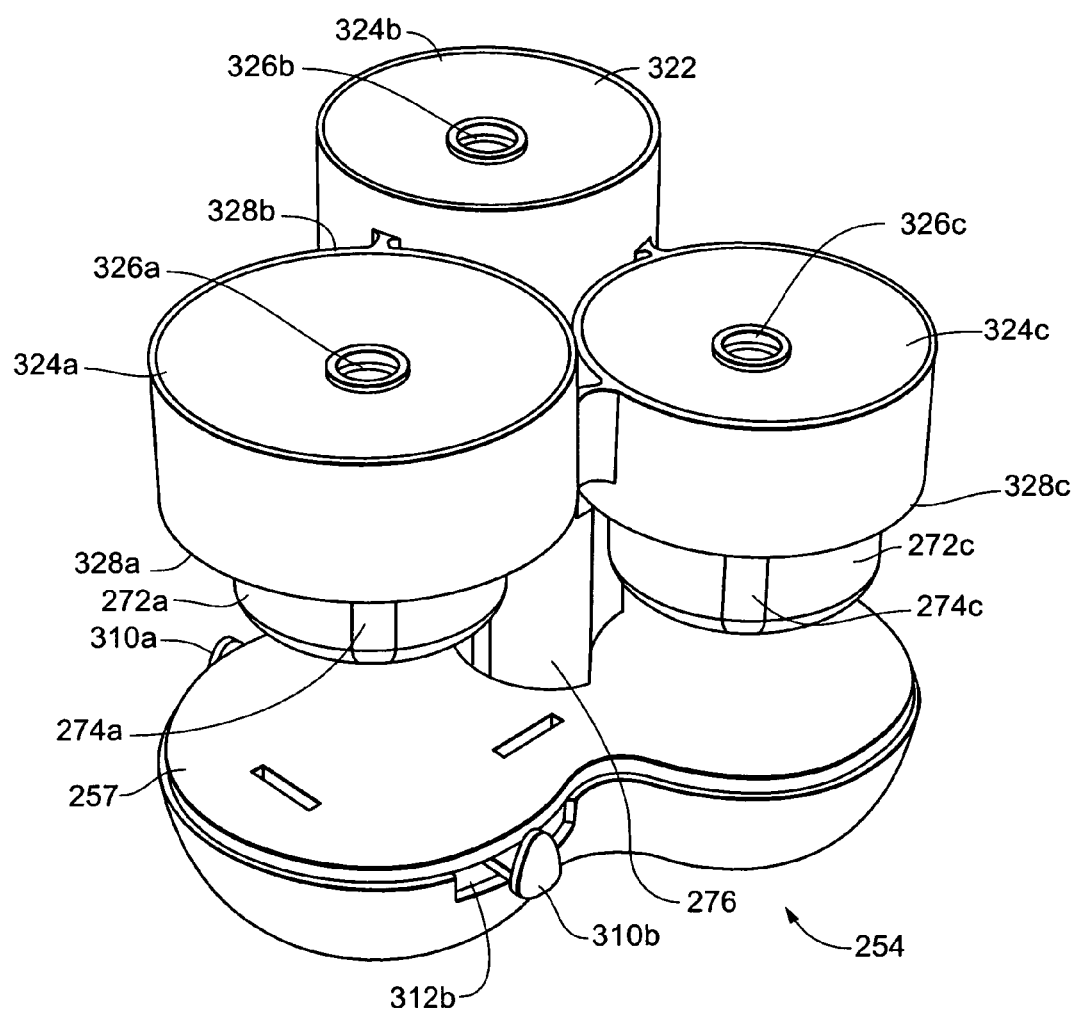
FIG. 14 is a top perspective view of the diffusion device of FIG. 13 illustrating a top cover removed therefrom.
Figure 14A:
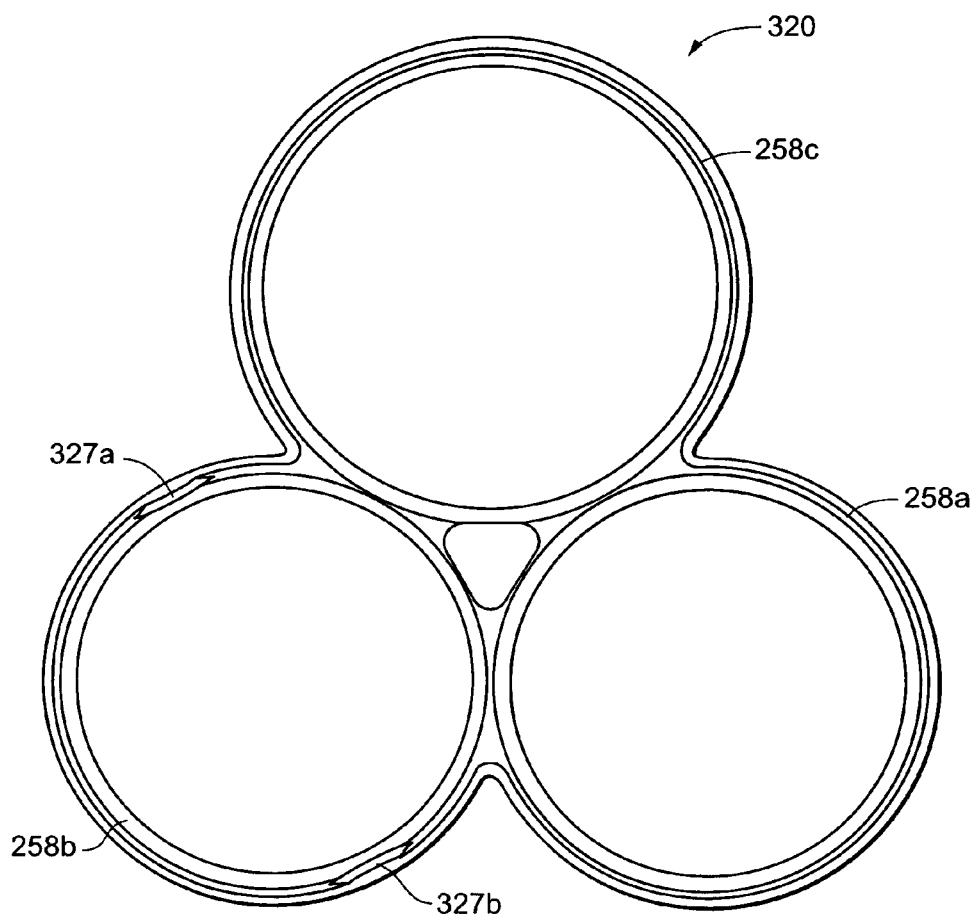
FIG. 14A is a bottom elevational view of a top cover of the diffusion device of FIG. 13.

As seen in FIGS. 14 and 14A, the tallest of the columns 258*a*-258*c* may include first and second opposing notches 327*a*, 327*b*. When the first integral portion 320 is removed from the bottom portion 254, the notches 327*a*, 327*b* catch on a lip portion 328*a*-328*c* of a respective cover portions 324*a*-324*c*, thereby preventing full removal of the first integral portion 320. Partial removal of the first integral portion 320 allows access to the inside of the device 250 to replace any containers 272*a*-272*c* therein. Optionally, sides of the column 258 having the notches 327*a*, 327*b* may be squeezed to release the notches 327*a*, 327*b* from the respective lip portion 328, thereby allowing removal of the first integral portion 320.

Similar to the embodiment of FIGS. 10-12, the top portion 252 of the embodiment of FIGS. 13-16 includes a support 276 integral with and extending perpendicularly from the bottom cover 257. A stationary pump assembly 279 is secured to the support 276 by a screw 281, but optionally may be secured by any known fastening means.

Figure 15:
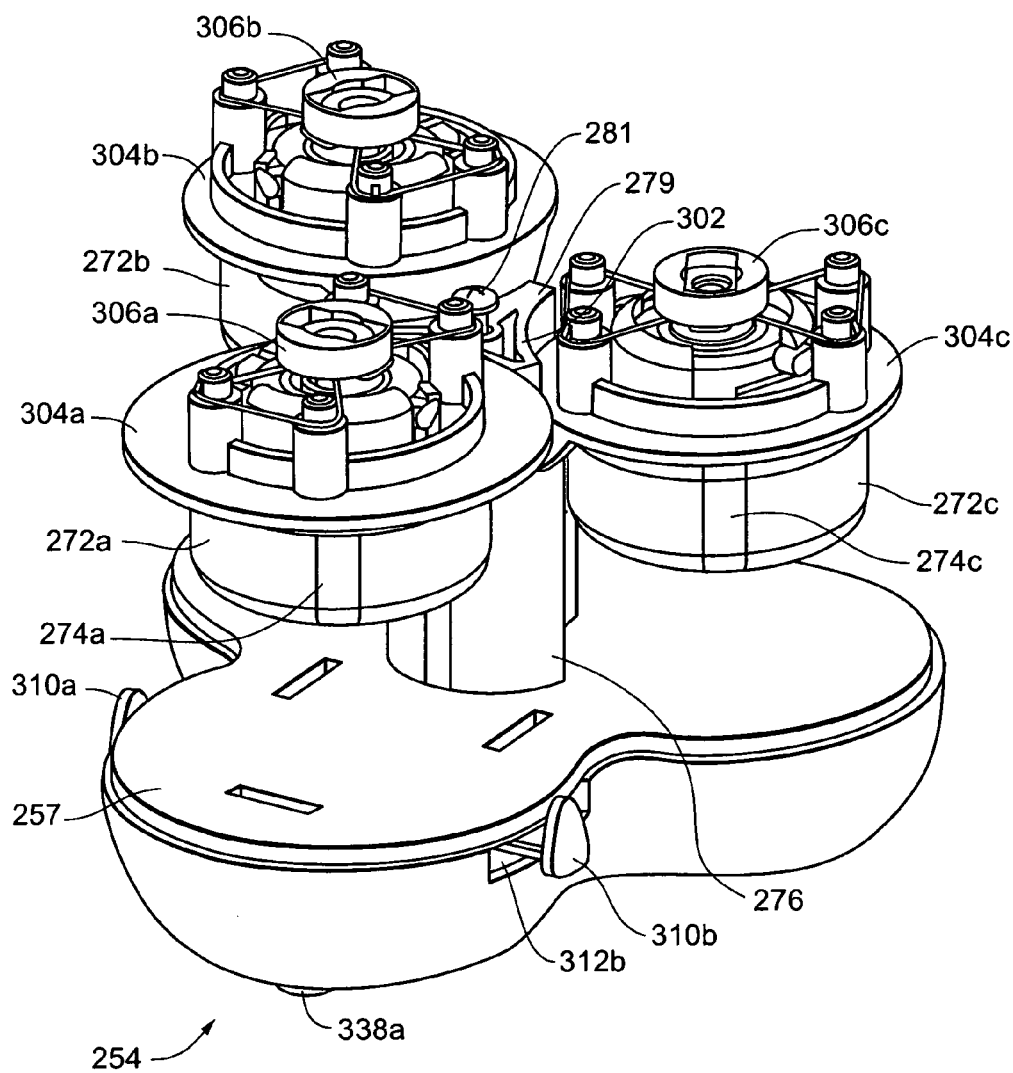
FIG. 15 is a top perspective view of the diffusion device of FIG. 14.
Figure 16:
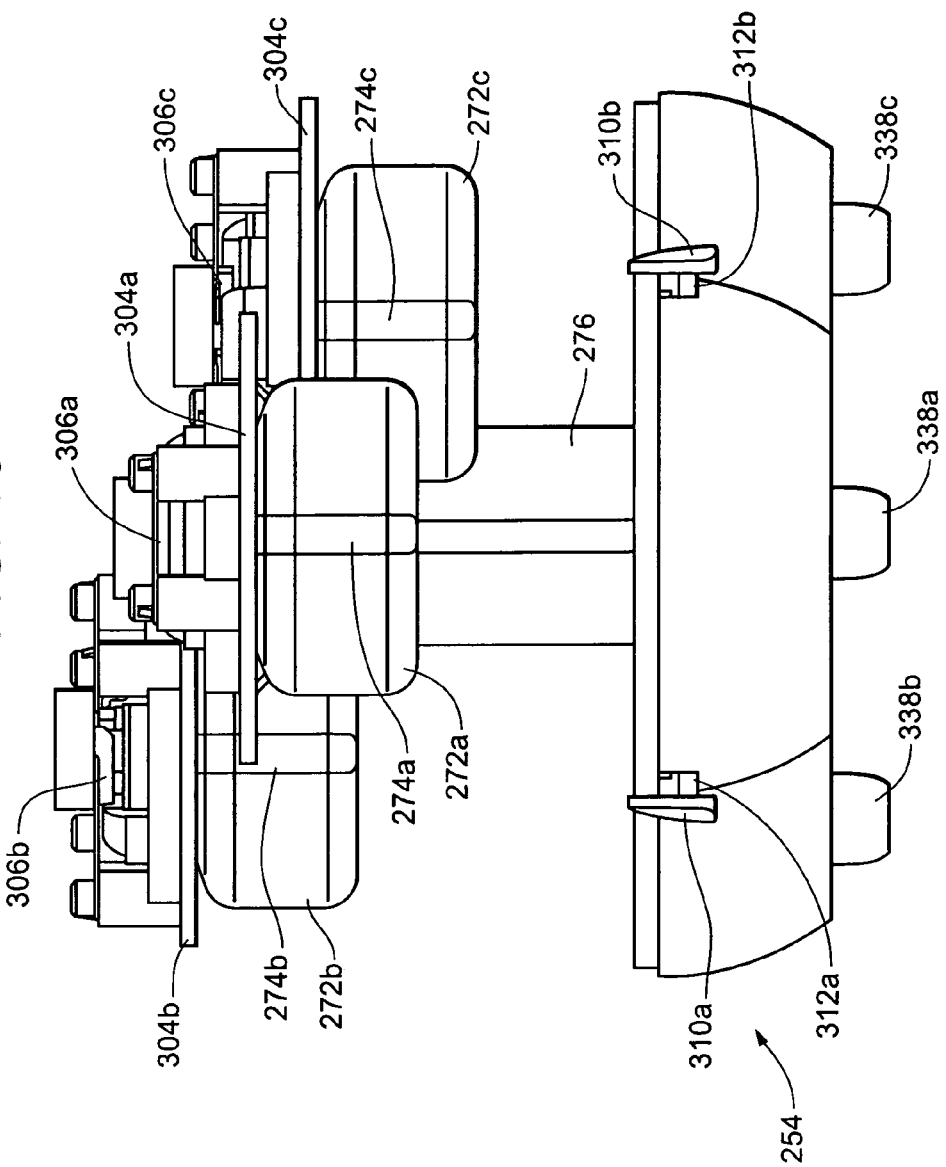
FIG. 16 is a side elevation view of the diffusion device of FIG. 15.

Referring to FIGS. 15 and 16, the pump assembly 279 includes a central portion 302 having first, second, and third arm portions 304*a*-304*c* extending from and integral with the central portion 302, wherein each of the arm portions 304*a*-304*c* includes a piezoelectric device 306*a*-306*c* respectively attached to a top portion thereof. When in use, the apertures 326*a*-326*c* in the cover portions 324*a*-324*c* are disposed above and aligned with the piezoelectric devices 304*a*-304*c*, respectively, to provide an outlet for active materials to be dispensed therefrom. The piezoelectric devices 306*a*-306*c* operate in the same manner as the piezoelectric devices 106*a*-106*c* described in connection with the embodiment of FIGS. 1-9.

Containers 272*a*-272*c* having wicks 274*a*-274*c* extending therefrom are inserted and removed from the arm portions 304*a*-304*c* in the same manner as described in connection with the embodiment of FIGS. 10-12.

An operating mode selector 310*a* and an emission frequency selector 310*b* both in the form of pivoting arms extend from the bottom portion 254 of the diffuser 250. The operating mode selector 310*a* controls the mode of diffusion of device 250 and extends through an aperture 312*a* in the bottom portion 254 of the diffuser 250. The operating mode selector 310*a* works similarly to the operating mode selector 110*a* of the embodiment of FIGS. 1-9. The emission frequency selector 310*b* controls the emission frequency of the diffusion device 250 and extends through another aperture 312*b* in the bottom portion 254 of the device 250. The emission 110 frequency selector 310*b* works similarly to the emission frequency selector 10*b* of the embodiment of FIGS. 1-9.

The bottom portion 254 contains the same components as shown and described in connection with the embodiment of FIGS. 1-9, and more specifically as seen and described in relation to FIGS. 8 and 9. Optionally, as best seen in FIG. 16, the device 250 may include feet 338*a*-338*c* for stabilization of the device 250.

A fourth embodiment of a diffusion device 350 of the present invention is depicted in FIGS. 17-23. The diffusion device 350 includes a top portion 352 and a bottom portion 354, wherein the top portion 352 includes a lid 355 and the bottom portion 354 includes a bottom cover 357. The lid 355 is attached to the bottom portion 354 by a hinge 359 (FIG. 19), wherein the lid 355 may be pivoted about the hinge 359 to open and close the lid 355 for access to contents of the bottom portion 354.

Referring now to FIGS. 20-23, the bottom portion 354 includes a base portion 361 that extends across a central portion of the bottom portion 354. The base portion 361 includes first, second, and third piezoelectric devices 406*a*-406*c* attached to a surface thereof and spaced from one another. First, second, and third apertures 363*a*-363*c* are disposed in the base portion 361 below the respective piezoelectric devices 406*a*-406*c*. First, second, and third containers 372*a*-372*c* having first, second, and third active materials disposed therein and first, second, and third wicks 374*a*-374*c* extending therefrom may be inserted into and secured by the first, second, and third apertures 363*a*-363*c*, such that the wicks 374*a*-374*c* are in contact with the respective piezoelectric devices 386*a*-386*c*. Preferably, the containers 372*a*-372*c* are secured into the first, second, and third apertures 363*a*-363*c*, as described in connection with the embodiment of FIGS. 10-12.

Figure 17:
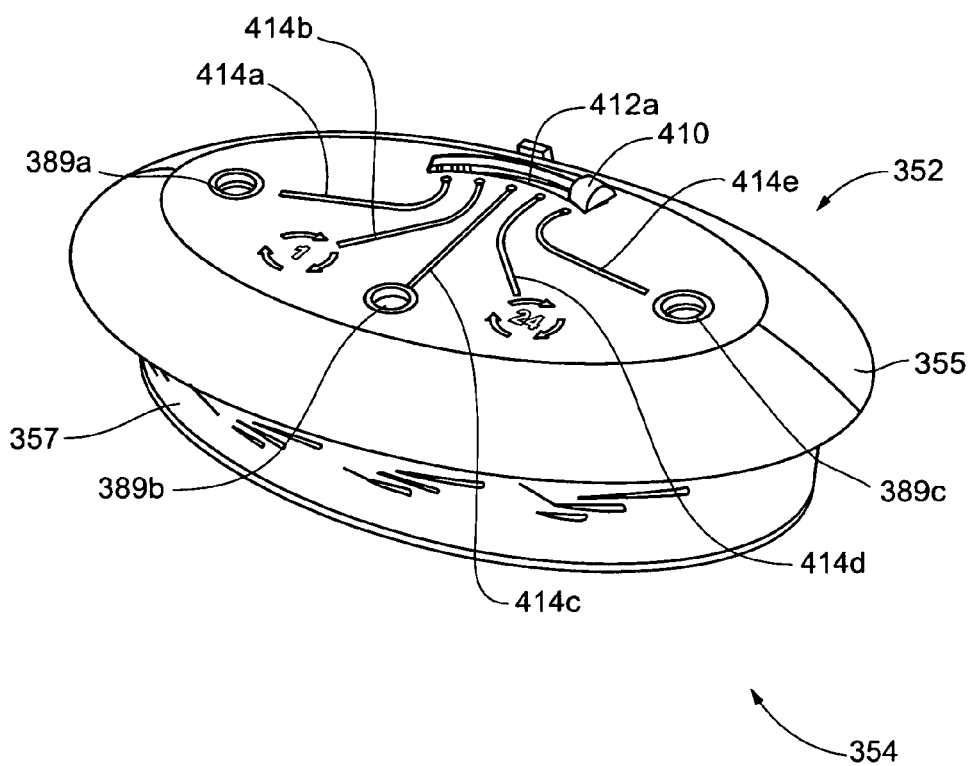
FIG. 17 is a top perspective view of a fourth embodiment of a diffusion device according to the present invention.
Figure 18:
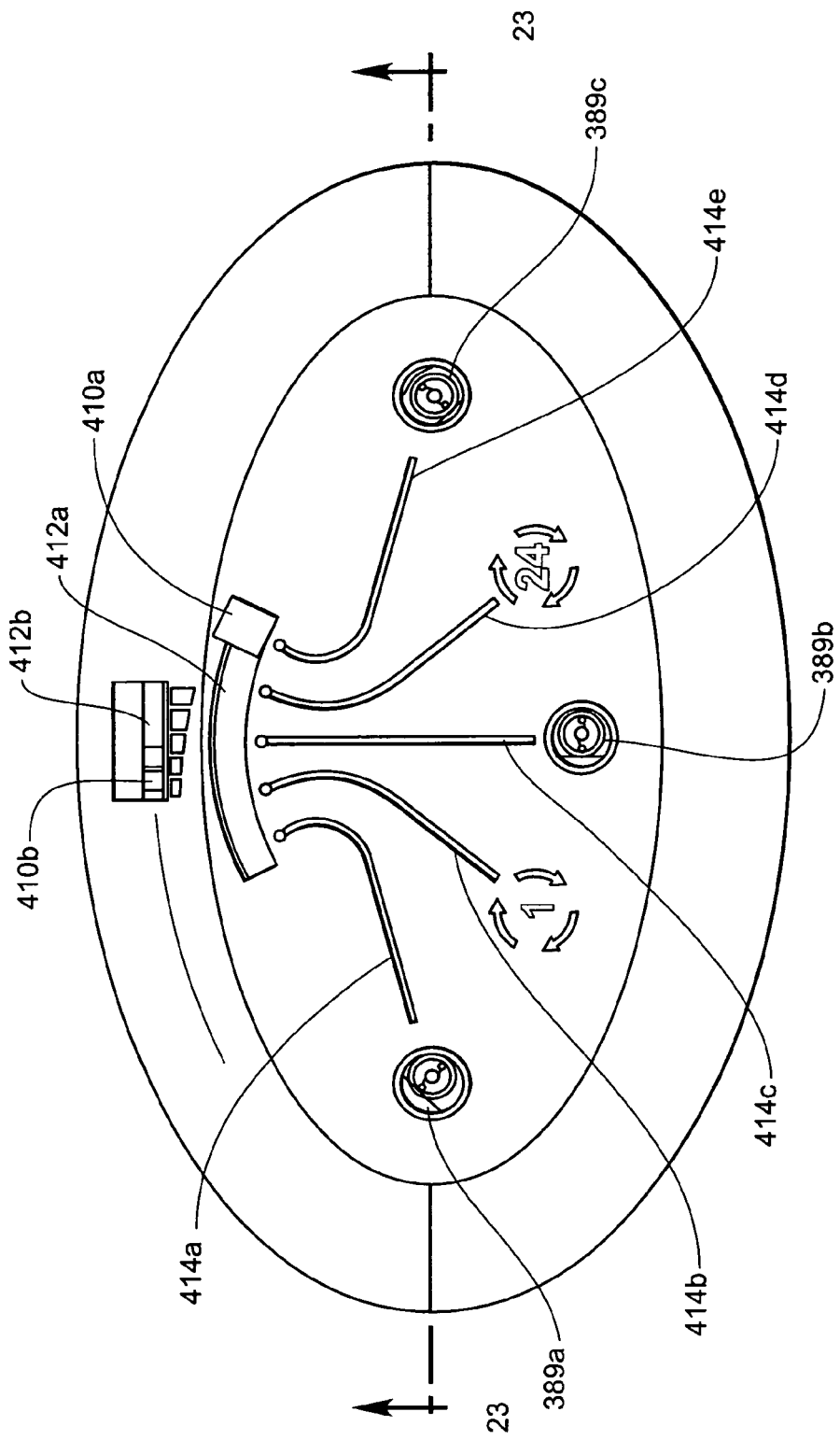
FIG. 18 is a plan view of the diffusion device of FIG. 17.
Figure 19:
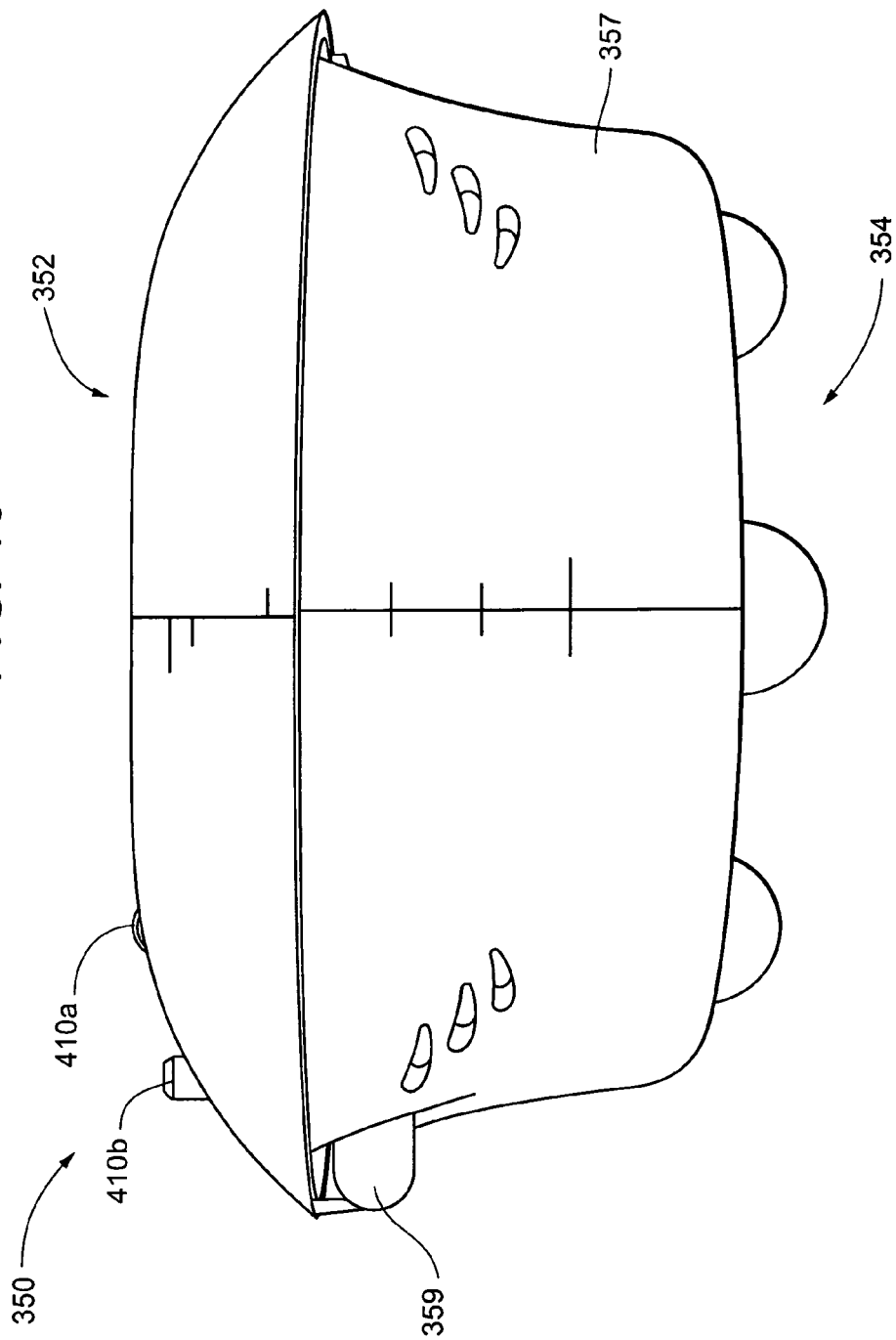
FIG. 19 is a side view of the diffusion device of FIG. 17.
Figure 20:
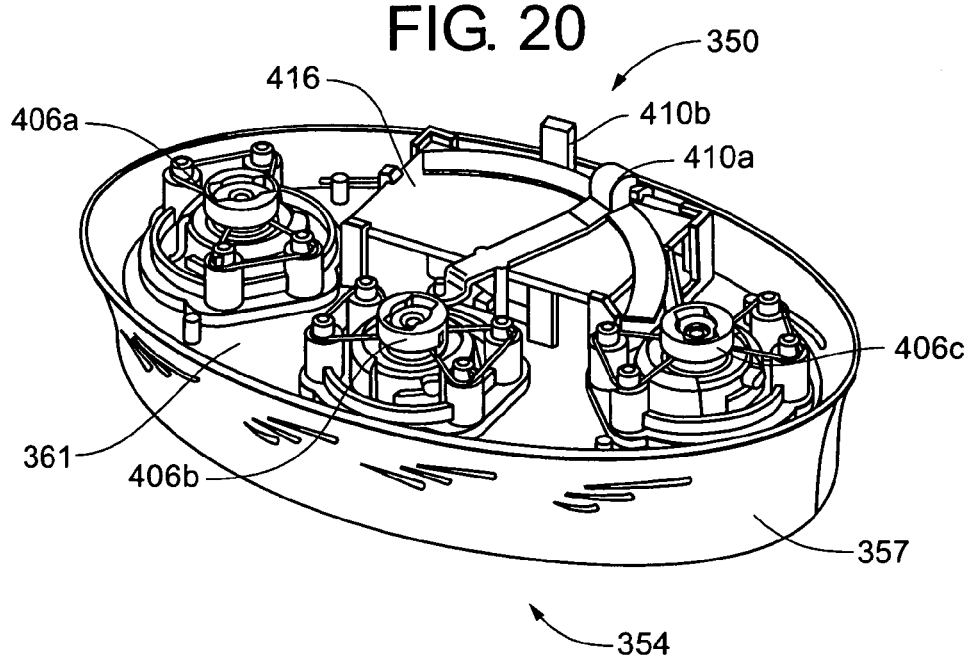
FIG. 20 is a top perspective view of the diffusion device of FIG. 17 illustrating a lid removed therefrom.
Figure 21:
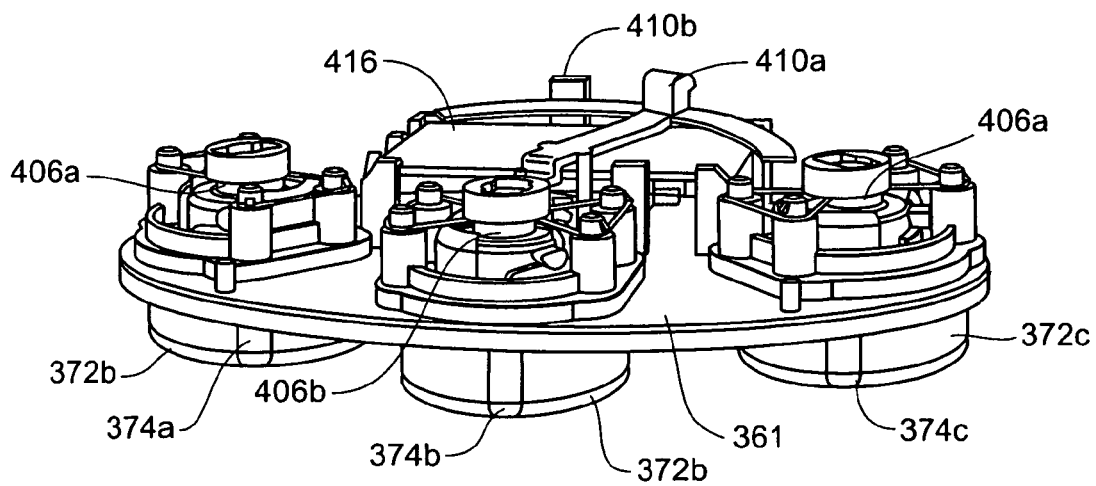
FIG. 21 is a top perspective view of the diffusion device of FIG. 17 illustrating a lid and bottom cover removed therefrom.
Figure 22:
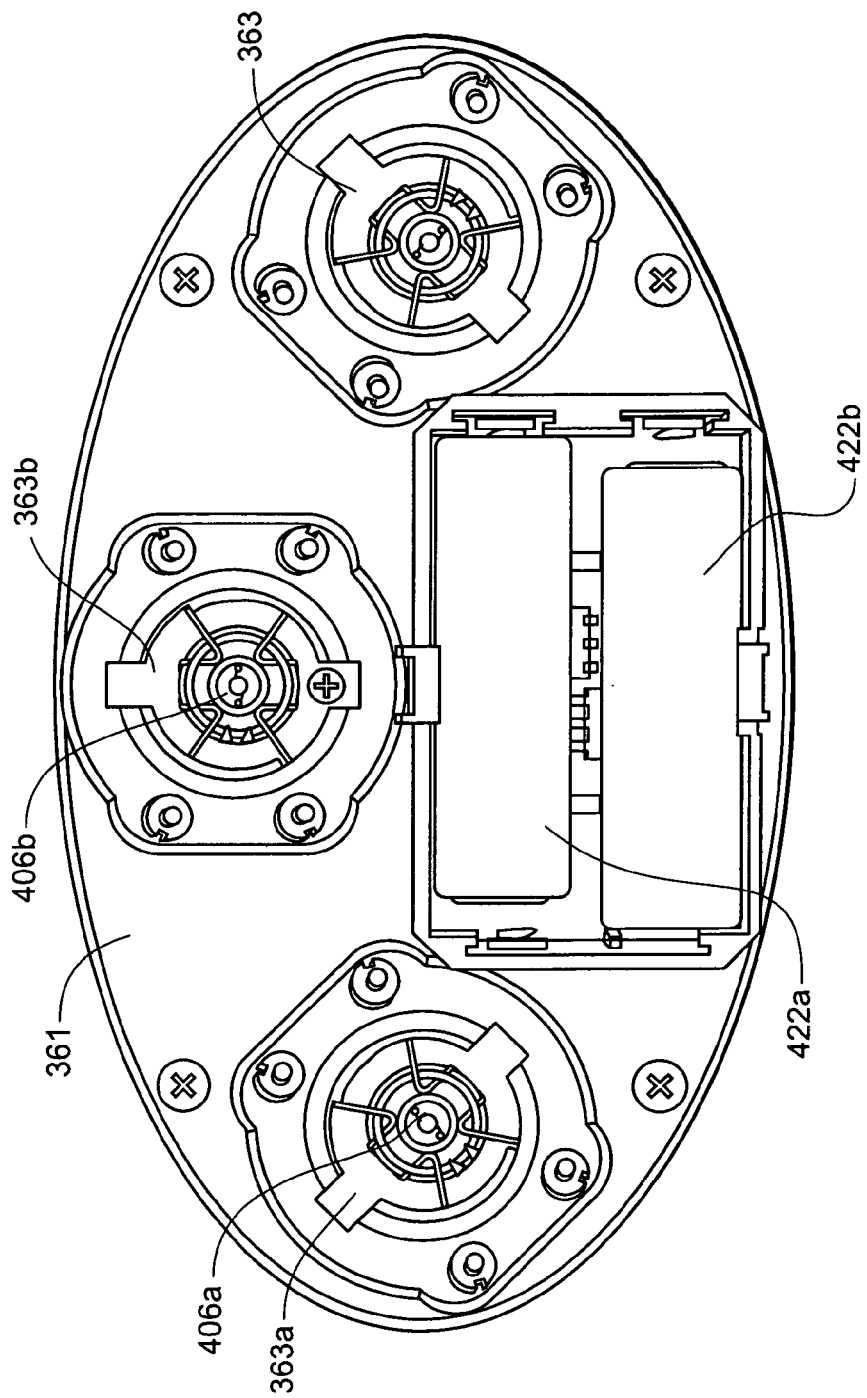
FIG. 22 is a bottom elevation view of a base portion of the diffusion device of FIG. 20.

As seen in FIGS. 17 and 18, the lid 355 includes first, second, and third emission apertures 389*a*-389*c* disposed therein and spaced from one another. The emission apertures 389*a*-389*c* are aligned with the wicks 374*a*-374*c* and piezoelectric devices 386*a*-386*c*. When one or more of the piezoelectric devices 386*a*-386*c* atomizes the active material in the respective container 372*a*-372*c*, aerosolized particles are projected upwardly and out the respective emission aperture 389*a*-389*c*. The piezoelectric devices 386*a*-386*c* operate as discussed in detail with respect to the embodiment of FIGS. 1-9.

An operating mode selector 410*a* extends through an apertures 412*a* disposed in the lid 355 and controls the operating mode of the device 350. The operating mode selector 410*a* is similar to and operates in a fashion similar to the embodiment of FIGS. 1-9. Illustratively, as seen in FIG. 17, the lid 355 may include indications as to what mode of emission is selected. For example, a first indicator 414*a* may indicate that the first active material from the first container 372*a* may be emitted from the device 350. A second indicator 414*b* may indicate that the device 350 will alternate between emitting the first, second, and third active materials from the first, second, and third containers 372a-372c, wherein the active material that is dispensed is changed every hour. Still a third indicator 414c may indicate that the second active material from the second container 372b may be emitted from the device 350. A fourth indicator 414d may indicate that the device 350 will alternate between emitting the first, second, and third active materials from the first, second, and third containers 372a-372c, wherein the active material that is dispensed is changed every 24 hours. A fifth indicator 414e may indicate that the third active material from the third container 372c may be emitted from the device 350. Any type of indicator or indicators may be used including, but not limited to, lines, dotted lines, dashed lines, arrows, or any other known indicator, or combinations thereof. Further, although the time periods of 1 hour and 24 hours are indicated on the lid 355, any time periods may be used, but preferred time periods are between about 1 minute and 24 hours.

An emission frequency selector 410b controls an emission frequency of the diffusion device 350 and extends through and moves along another aperture 412b in the lid 355. The emission frequency selector 410b is similar to and operates in a manner similar to the emission frequency selector 10b discussed with respect to the embodiment of FIGS. 1-9. As seen in FIG. 18, the lid 355 may also have indications disposed adjacent the aperture 412b to indicate the selected intensity level.

Figure 23:
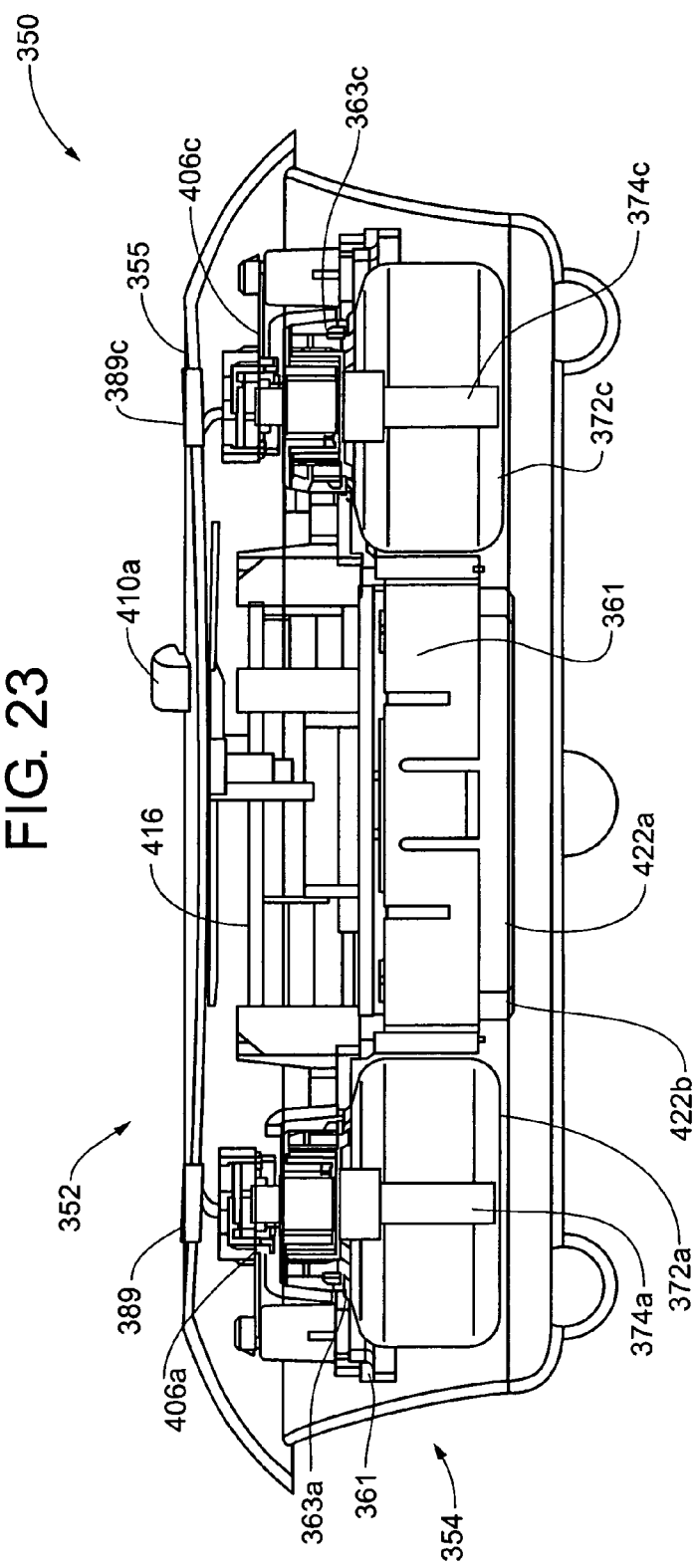
FIG. 23 is a cross-sectional view taken generally along the lines 23-23 of FIG. 18.

As seen in FIGS. 20-23, a PCB 416 is connected to the base portion 361. The components of the PCB 416 are the same as those disclosed with respect to the embodiment of FIGS. 1-9, except that they are on the underside of the PCB 416 to protect the components from damage when a user accesses the interior of the bottom portion 354. As with the other embodiments disclosed herein, the device 350 may include one or more batteries 422a, 422b for providing power to the piezoelectric devices 406a-406c. The batteries are preferably disposed below the base portion 361, as seen in FIGS. 23 and 24.

In the embodiment of FIGS. 17-23, when the user desires to replace one or more batteries 422a, 422b and/or one or more containers 372a-372c, the user must first open the lid 355 of the device 350. The base portion 361 is attached to the lid 355 by a plurality of screws 424. Therefore, as the lid 355 is rotated about the hinge 359 to an open position, the base portion 361, and thus all of the components of the device 450, are rotated with the lid 355. At this point, the containers 372a-372c and/or batteries 422a, 422b, which are accessible, may be and replaced. After the user has replaced the necessary components, the lid 355, and thus the base portion 361 and other attached components, may be rotated into a closed position.

In any of the embodiments herein, an LED may be incorporated into the device to provide an indication to the user. For example, any of the embodiments may include an LED protruding from the bottom portion of the device, wherein the LED indicates an on/off condition of the device or a battery power of the device. In another example, the embodiment of FIGS. 17-23 may optionally include one or more LED(s) protruding from the lid 355, wherein the LED(s) may indicate an on/off condition of the device, a battery power of the device, an operation of a particular pump, and/or the current operating mode of the device.

Figure 24:
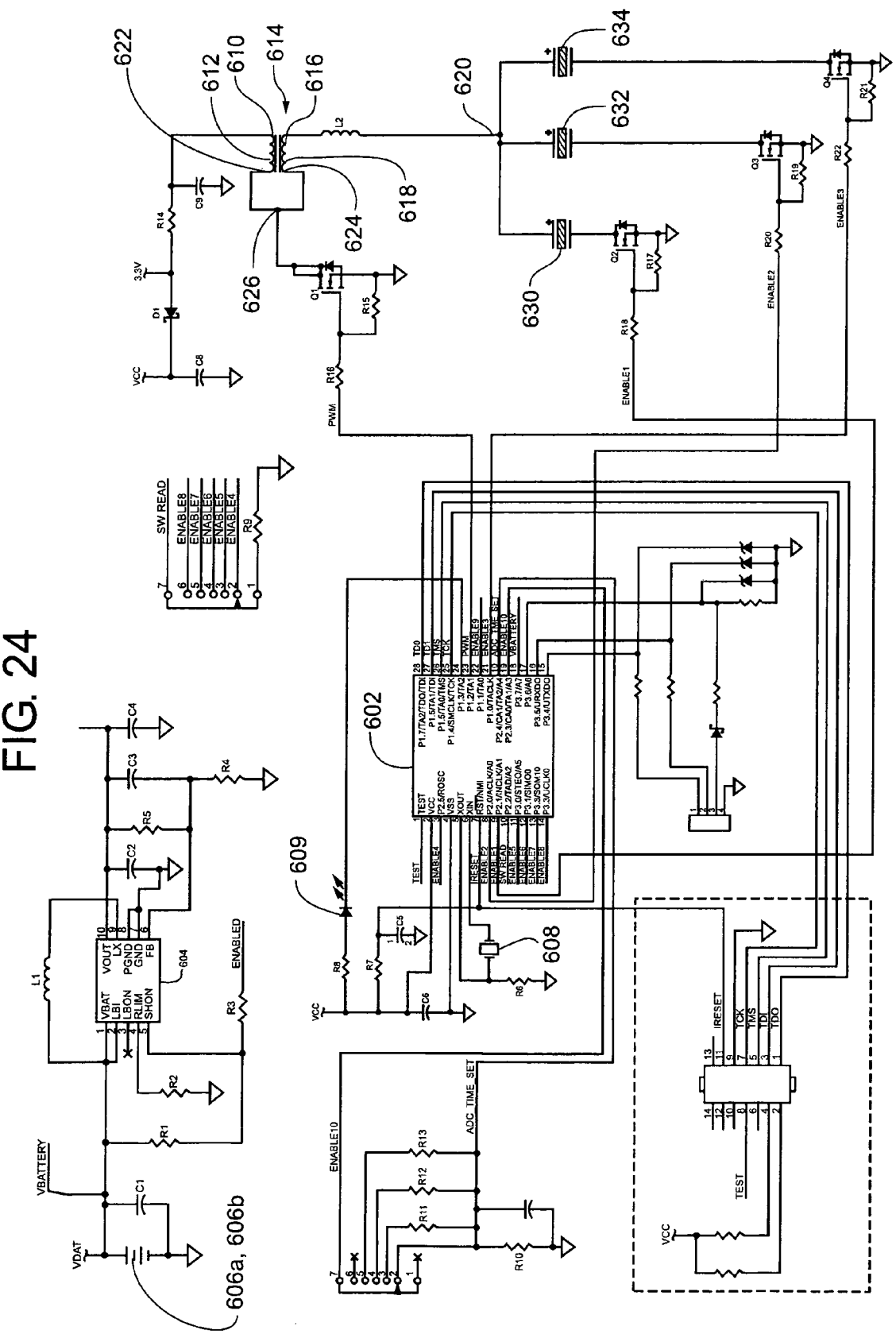
FIG. 24 is a diagram of an exemplary circuit for controlling one or more components of any of the diffusion devices of the present invention.

Referring next to FIG. 24, circuitry 600 for operating any of the diffusion devices of the present invention in accordance with a selected mode and selected emission frequency includes a first integrated circuit (IC) 602, which may be an application specific integrated circuit (ASIC) or a microprocessor, and a further integrated circuit 604, preferably a high efficiency boost regulator. The IC 602 may comprise an MSP430F1222 integrated circuit manufactured by Texas Instruments of Dallas, Tex., whereas the integrated circuit 604 may comprise an SP6648 integrated circuit manufactured by Sipex Corporation of Milpitas, Calif. The integrated circuit 604 receives battery power from two AA size batteries 606a, 606b and develops a 3.3 volt reference level in conjunction with resistors R1-R5, capacitors C1-C4, and inductor L1.

The IC 602 includes an internal oscillator that is controlled by a crystal 608 coupled between pins 5 and 6 of the IC 602. A resistor R6 is coupled between one end of the crystal 608 and ground potential. In addition, the IC 602 receives the voltage $V_{cc}$ and ground potential at pins 2 and 4 thereof, respectively. A pin 7 of the integrated circuit 602 is coupled to a junction between a resistor R7 and a capacitor C5. A further end of the resistor R7 is coupled to $V_{cc}$ and a capacitor C6 is coupled between $V_{cc}$ and ground. A pin 24 of the integrated circuit 602 is coupled to an LED 609 and a resistor R8, wherein an end of the resistor R8 is also coupled to $V_{cc}$. The IC 602 receives a signal SW_READ at a pin 10 via a resistor R9 that is connected to ground. The signal SW_READ indicates the position of the selector 110a. More specifically, the signal SW_READ indicates which of pins 3 and 11-14 (ENABLE4, ENABLE5, ENABLE6, ENABLE7, and ENABLE8, respectively) is coupled to pin 10 of the IC 602. The signal SW_READ may be read in conjunction with signals ENABLE4, ENABLE5, ENABLE6, ENABLE7, and ENABLE8.

The IC 602 also receives a signal ADC_TIME_SET at pin 20, wherein the signal ADC_TIME_SET indicates the corresponding time interval for the position of the selector 110b that has been selected. Signal ADC_TIME_SET may be read in conjunction with signal ENABLE 10, wherein ADC_TIME_SET is an analog input pin that reads different voltages created by the resistor network including resistors R10-R13 depending on the position of the selector 10b.

A Schottky diode D1 is coupled between the 3.3V reference and $V_{cc}$. A further capacitor C8 is coupled between $V_{cc}$ and ground potential. Capacitor C9 is connected to a first terminal 610 of a primary winding 612 of a transformer 614. A first terminal 616 of a secondary winding 618 of the transformer 614 is coupled through an inductor L2 to a junction 620. Second terminals 622 and 624 of the primary and secondary windings 612, 618, respectively are coupled to a further junction 626. The junction 626 is coupled by a field effect transistor (FET) Q1 to ground. A biasing resistor R15 is coupled between a gate and a source of the FET Q1 and the gate receives a control signal PWM through a resistor R16. The signal PWM is developed at a pin 23 of the IC 602.

The junction 620 is coupled to first terminals of piezoelectric elements 630, 632, 634. The piezoelectric element 630 comprises the driving element for the piezoelectric device 86a, the piezoelectric element 632 comprises the driving element for the piezoelectric device 86b, and the piezoelectric element 634 comprises the driving element for the piezoelectric device 86c. Second terminals of the piezoelectric elements 630, 632, 634 are coupled by FET's Q2, Q3, and Q4, respectively, to ground. A biasing resistor R17 is coupled between the gate and the source of the FET Q2 and the gate of the FET Q2 receives a control signal ENABLE1 through a resistor R18. Similarly, a biasing resistor R19 is coupled between the gate and the source of the FET Q3 and a control signal ENABLE2 is coupled through a resistor R20 to the gate of the FET Q3. Still similarly, another biasing resistor R21 is coupled between the gate and the source of the FET Q4 and a control signal ENABLE3 is coupled through resistor R22 to the gate of the FET Q4. The control signals ENABLE1, ENABLE2, and ENABLE3 are developed at pins 9, 8 and 21, of the IC 602.

Referring next to the flow chart of FIG. 24, the IC 602 is programmed to cause any of the devices of the present invention to operate in accordance with a selected mode and emission frequency. As seen in FIG. 25, operation commences at a block 700 which checks to determine whether the selector 110a is in a first position. If this is found to be the case, control passes to a block 702 that selects first mode for operation. On the other hand, if the block 700 determines that the selector 110a is not in the first position, then a block 704 checks to determine whether the selector 110a is in the second position. If this is the case, then a block 706 selects a second mode of operation. If the block 704 determines that the selector 110a is not in the second position, then a block 708 checks to determine whether the selector 10a is in the third position. If this is the case, then block 710 selects a third mode of operation. If the block 708 determines that the selector 110a is not in the third position, then a block 712 checks to determine whether the selector 110a is in a fourth position. If selector 110a is in the fourth position, then block 714 selects a fourth mode of operation. If block 712 determines that selector 110a is not in the fourth position, then it has been determined that the selector 110a is in the fifth position and a block 716 selects a fifth mode of operation. The IC 602 senses the position of the selector 110a by checking SW_READ, which, as noted above, is provided to the pin 10 of the IC 602 in conjunction with ENABLE4-ENABLE8. The IC also senses the position of the selector 110b by checking ADC_TIME_SET, which, as noted above, is provided to the pin 20 of the IC 602 in conjunction with ENABLE10.

Once the mode has been selected, a block 718 checks the position of the selector 110b in a fashion similar to the blocks 700-716 described above to determine the selected emission frequency. Once the emission frequency has been determined, a block 718 causes the IC 602 to develop the signals PWM, ENABLE1, ENABLE2, and ENABLE3, in turn to cause the piezoelectric elements 630, 632, 634 to be energized in accordance with the selected mode of operation and emission frequency. Specifically, a high frequency pulse-width modulated waveform having a frequency between about 130 kHz and about 165 kHz is provided as the control signal PWM, thereby causing the FET Q1 to rapidly turn on and off, thereby causing high frequency alternating current power to be provided to the junction 620. When the piezoelectric element 630 is to be operated, a high state signal is provided as the signal ENABLE1, thereby turning on the FET Q2. When the piezoelectric element 632 is to be operated, a high state signal is provided as the signal ENABLE2, thereby turning on the FET Q3. When the piezoelectric element 634 is to be operated, a high state signal is provided as the signal ENABLE3, thereby turning on the FET Q4.

In summary, a user may operate any of the devices as described herein to emit a selected one of three different active materials for a particular period of time at a selected emission frequency, or may cause the unit to alternate between emissions of different active materials at a selected emission frequency.

Although the embodiments as discussed herein are shown and described as being powered by a direct current source, such as batteries, other alternating current power sources are contemplated. For example, any of the devices as described herein may operate on household power via a plug extending from the device, wherein a cord may be coupled to the plug and the device. Still optionally, the plug may be mounted directly to the device for insertion into a household power source.

Illustratively, the types of liquid active materials described herein may be, for example, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing active material, an air-freshener, a deodorizer, or the like, and combinations thereof. The present application contemplates the use of the same or different active materials and/or the same or different types of active materials. For example, container 72a may include a fragrance therein, container 72b may include an insecticide, and container 72c may include a disinfectant. Alternatively, in another example, the container 72a may include a strawberry fragrance, the container 72b may include a vanilla fragrance, and the container 72c may include an orange fragrance. As such, any combination of types of liquid active materials may be utilized in any of the containers of any of the embodiments disclosed herein.

Optionally, the piezoelectric-type devices as disclosed herein may be replaced by any other known diffuser devices. For example, the piezoelectric devices may be replaced by heated-wick type devices, passive devices, aerosol devices, and the like, and combinations thereof.

Illustratively, the diffusion devices are made of a thermoplastic material, preferably polypropylene, and are injection molded, although the device may be made of any other suitable material. Various components of the embodiments of diffusion devices are fastened together. As such, any fastening means may be used, including, but not limited to heat-staking or any other suitable fastening means, including, for example, rivets, press fit, snap fit, screws, ultrasonic welding, adhesives, or the like and combinations thereof.

The containers of the present invention are replaceable when empty or whenever a user desires a new active material. One or more containers may be removed and replaced at the same time. Optimally, the active material in all three containers would be used up in a similar timeframe, thereby necessitating the removal and replacement of all three containers at one time. As such, containers having active materials therein may be sold in three-packs that may have a theme. Optionally, containers may be sold individually for purchase by a consumer.

Although the embodiments disclosed herein depict diffusion devices with three piezoelectric devices and three containers, the features of any of the embodiments as disclosed herein may be incorporated into a diffusion device having any number of piezoelectric devices and containers. In one example, a diffusion device may have only one piezoelectric device and one container. In another example, a diffusion device may have two piezoelectric devices and two containers.

INDUSTRIAL APPLICABILITY

The diffusion devices of the present invention can be used to automatically dispense multiple active materials over an extended period of time, with the added advantage that the frequency of dispersion and the mode of operation may be adjusted. Various methods of inserting containers may be utilized to enable a purchaser of such a diffusion device to easily remove and replace the containers.

Numerous modifications will be apparent to those skilled in the art in view of the foregoing description. Accordingly, this description is to be construed as illustrative only and is presented for the purpose of enabling those skilled in the art to make and use the invention and to teach the best mode of carrying out same. All patents and other references cited herein are incorporated by reference in their entirety. The exclusive rights to all modifications which come within the scope of the appended claims are reserved.

We claim:

1. A diffusion device, comprising:
   a bottom portion having a bottom cover disposed thereon;
   a top portion having a top cover disposed atop the bottom portion;
   a pump assembly disposed between the top cover and the bottom cover;
   first, second, and third arm portions extending from the pump assembly, wherein the first, second, and third arm portions include first, second, and third piezoelectric devices, respectively, attached thereto; and
   first, second, and third containers having first, second, and third, wicks respectively, wherein the first, second, and third containers are manually attached to the first, second, and third arm portions of the pump assembly such that the first, second, and third wicks are disposed adjacent the first, second, and third piezoelectric devices, respectively, when the containers are inserted into the device.

2. The diffusion device of claim 1, further including a support that is secured to and extends from the bottom cover and wherein the support connects the bottom portion and the pump assembly.

3. The diffusion device of claim 2, wherein the pump assembly is connected to the support by a screw.

4. The diffusion device of claim 2, wherein the pump assembly is spring-loaded and slidingly connected to the support.

5. The diffusion device of claim 1, further including an operating mode selector that is adapted to control the mode of operation of the device and which includes five positions, wherein the device includes at least first and second modes of operation.

6. The diffusion device of claim 5, wherein the modes of operation may be selected from the group of modes comprising: emitting the first active material, emitting the second active material, emitting the third active material, alternating between the first, second, and third active materials at a first predetermined duration, alternating between the first, second, and third active materials at a second predetermined duration, increasing the emission of one or more active materials over time, decreasing the emission of one or more active materials over time, and periodically discontinuing emission of one or more active materials over time.

7. The diffusion device of claim 5, further including an emission frequency selector that includes five positions that allow the device to be set at one of five different dwell times, where the dwell time is the time between sprays.

8. The diffusion device of claim 1, further including first, second, and third containers having first, second, and third wicks, respectively, wherein the first, second, and third wicks are disposed adjacent the first, second, and third piezoelectric devices when the top cover is disposed atop the bottom portion.

9. The diffusion device of claim 8, wherein the first, second, and third wicks are not disposed adjacent the first, second, end third piezoelectric devices when the top cover is removed from the bottom portion.

10. The diffusion device of claim 1, further including at least one battery that provides power to energize the piezoelectric devices.

11. The diffusion device of claim 10, further including a door in a bottom surface of the bottom portion, wherein the door may be opened to insert and remove the at least one battery.

12. The diffusion device of claim 1, wherein the top cover is formed into three columns and wherein one of the columns includes first and second flexible portions comprising flaps and wherein pressure may be exerted on the first and second flexible portions to remove the top cover from the diffusion device.

13. A diffusion device, comprising:
   a top portion having a top cover and a bottom portion having a bottom cover, wherein the top cover is disposed atop the bottom cover, thereby forming a cavity therebetween;
   a container disposed in cavity, wherein the container includes an active material therein and a wick extending therefrom;
   a spring-loaded pump assembly slidingly connected to the bottom cover and including a piezoelectric element extending therefrom;
   wherein when the top cover is inserted over the spring-loaded pump assembly, the pump assembly moves downwardly such that the piezoelectric element is moved into contact with the wick extending from the container and when the cover is removed, the pump assembly moves upwardly and out of contact with the wick.

14. The diffusion device of claim 13, wherein the top cover and the bottom cover form first, second, and third cavities therebetween and wherein first, second, and third containers having first, second, and third active materials therein and first, second, and third wicks, respectively, extending therefrom are disposed within the first, second, and third cavities, respectively.

15. The diffusion device of claim 14, wherein the spring-loaded pump assembly includes first, second, and third piezoelectric elements extending therefrom that are moved into contact with the first, second, and third wicks when the top cover is inserted over the spring-loaded pump assembly.

16. The diffusion device of claim 14, wherein the first, second, and third active materials are different.

17. A diffusion device, comprising:
   a bottom portion having a bottom cover disposed thereon;
   a top portion having a top cover disposed atop the bottom portion;
   a pump assembly disposed between the top cover and the bottom cover;
   first, second, and third arm portions extending from the pump assembly, wherein the first, second, and third arm portions include first, second, and third piezoelectric devices, respectively, attached thereto; and
   an operating mode selector that is adapted to control the mode of operation of the device and which includes five positions, wherein the device includes at least first and second modes of operation.

18. The diffusion device of claim 17, wherein the modes of operation may be selected from the group of modes comprising: emitting the first active material, emitting the second active material, emitting the third active material, alternating between the first, second, and third active materials at a first predetermined duration, alternating between the first, second, and third active materials at a second predetermined duration, increasing the emission of one or more active materials over time, decreasing the emission of one or more active materials over time, and periodically discontinuing emission of one or more active materials over time.

19. The diffusion device of claim 17, further including an emission frequency selector that includes five positions that allow the device to be set at one of five different dwell times, where the dwell time is the time between sprays.

* * * * *